(12) United States Patent
Nathwani et al.

(10) Patent No.: US 10,124,041 B2
(45) Date of Patent: *Nov. 13, 2018

(54) METHODS OF DELIVERING FACTOR VIII ENCODING NUCLEIC ACID SEQUENCES

(71) Applicants: UCL BUSINESS PLC, London (GB); ST. JUDE CHILDREN'S RESEARCH HOSPITAL, Memphis, TN (US)

(72) Inventors: Amit Nathwani, London (GB); Jenny McIntosh, London (GB); Edward Tuddenham, London (GB); Andrew Davidoff, Memphis, TN (US)

(73) Assignees: UCL BUSINESS PLC, London (GB); ST. JUDE CHILDREN'S RESEARCH HOSPITAL, Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/254,984

(22) Filed: Sep. 1, 2016

(65) Prior Publication Data

US 2017/0049859 A1  Feb. 23, 2017

Related U.S. Application Data

(63) Continuation of application No. 14/407,008, filed as application No. PCT/GB2013/051551 on Jun. 12, 2013, now Pat. No. 9,447,168.

(30) Foreign Application Priority Data

Jun. 12, 2012 (GB) .................................. 1210357.8

(51) Int. Cl.
| | | |
|---|---|---|
| *C12N 15/05* | (2006.01) | |
| *A61K 38/37* | (2006.01) | |
| *C07K 14/755* | (2006.01) | |
| *A01K 67/027* | (2006.01) | |
| *A61K 48/00* | (2006.01) | |

(52) U.S. Cl.
CPC .......... *A61K 38/37* (2013.01); *A01K 67/0275* (2013.01); *C07K 14/755* (2013.01); *A01K 2227/105* (2013.01); *A01K 2267/01* (2013.01); *A61K 48/00* (2013.01)

(58) Field of Classification Search
None
See application file for complete search history.

(56) References Cited

U.S. PATENT DOCUMENTS

| | | |
|---|---|---|
| 6,103,526 A | 8/2000 | Smith et al. |
| 6,200,560 B1 | 3/2001 | Couto et al. |
| 6,221,349 B1 | 4/2001 | Couto et al. |
| 6,383,794 B1 | 5/2002 | Mountz et al. |
| 6,818,439 B1 | 11/2004 | Jolly et al. |
| 6,924,365 B1 | 8/2005 | Miller et al. |
| 7,351,577 B2 | 4/2008 | Couto et al. |
| 7,351,813 B2 | 4/2008 | Miao et al. |
| 7,572,619 B2 | 8/2009 | Hauser et al. |
| 8,030,065 B2 | 10/2011 | Gray |
| 8,198,421 B2 | 6/2012 | Samulski |
| 9,447,168 B2 * | 9/2016 | Nathwani .......... A01K 67/0275 |
| 9,504,762 B2 | 11/2016 | Colosi et al. |
| 2003/0148506 A1 | 8/2003 | Kotin et al. |
| 2007/0042462 A1 | 2/2007 | Hildinger |
| 2008/0131403 A1 | 6/2008 | Wang et al. |
| 2009/0017533 A1 | 1/2009 | Selden et al. |
| 2009/0175833 A1 | 7/2009 | Dore-Duffy et al. |
| 2010/0284971 A1 | 11/2010 | Samulski |
| 2013/0024960 A1 | 1/2013 | Nathwani et al. |
| 2017/0049859 A1 * | 2/2017 | Nathwani .......... A01K 67/0275 |

FOREIGN PATENT DOCUMENTS

| | | |
|---|---|---|
| JP | 2003-530093 A | 10/2003 |
| WO | WO-01/98482 A2 | 12/2001 |
| WO | WO-2005/052171 A2 | 6/2005 |
| WO | WO-2007/148971 A2 | 12/2007 |
| WO | WO-2009/014445 A2 | 1/2009 |
| WO | WO-2009/017533 A1 | 2/2009 |
| WO | WO-2010/111414 A1 | 9/2010 |
| WO | WO-2011/005968 A1 | 1/2011 |
| WO | WO-2011/139629 A2 | 11/2011 |

OTHER PUBLICATIONS

Alam et al., Lung surfactant protein B promoter function is dependent on the helical phasing, orientation and combinatorial actions of cis-DNA elements, Gene, 282:103-11 (2002).
Bantel-Schaal et al., Human adeno-associated virus type 5 is only distantly related to other known primate helper-dependent parvoviruses. J. Virol. 73: 939-47 (1999).
Cerullo et al., Correction of murine hemophilia A and immunological differences of factor VIII variants delivered by helper-dependent adenoviral vectors. Mol. Ther. 15: 2080-7 (2007).
Chao et al., Expression of human factor VIII by splicing between dimerized AAV vectors. Mol. Ther. 5: 716-22 (2002).
Chen et al., Enhanced factor VIII heavy chain for gene therapy of hemophilia A. Mol. Ther. 17: 417-24 (2009).
Chiorini et al., Cloning and characterization of adeno-associated virus type 5. J. Virol. 73: 1309-19 (1999).
Chiorini et al., Cloning of adeno-associated virus type 4 (AAV4) and generation of recombinant AAV4 particles. J. Virol. 71: 6823-33 (1997).

(Continued)

*Primary Examiner* — Hope Robinson
(74) *Attorney, Agent, or Firm* — Marshall, Gerstein & Borun LLP

(57) ABSTRACT

There is provided a nucleic acid molecule comprising a nucleotide sequence encoding a factor VIII protein, wherein a B domain portion of the factor VIII protein is encoded by a nucleotides sequence between 90 and 111 nucleotides in length and has an amino acid sequence that is at least 85% identical to SEQ ID NO: 4 which comprises six asparagine residues. Also provided is a factor VIII protein, a vector comprising the above nucleic acid molecule, a host cell, a transgenic animal, a method of treating Haemophilia A, and a method for the preparation of a parvoviral gene delivery vector.

8 Claims, 5 Drawing Sheets

(56) References Cited

OTHER PUBLICATIONS

De Simone et al., Cis- and trans-acting elements responsible for the cell-specific expression of the human alpha 1-antitrypsin gene, EMBO J., 6(9):2759-66 (1987).
Edelstein, Gene therapy clinical trials worldwide 1989-2004-an overview, J. Gene Med., 6:597-602 (2004).
Fagone et al., Systemic errors in quantitative polymerase chain reaction titration of self-complementary adeno-associated viral vectors and improved alternative methods. Hum. Gene Ther. Meth. 23: 1-7 (2012).
Gao et al., Novel adeno-associated viruses from rhesus monkeys as vectors for human gene therapy. Proc. Natl. Acad. Sci. USA, 99: 11854-9 (2002).
Ghosh et al., Expanding adeno-associated viral vector capacity: a tale of two vectors, Biotechnol. Genet. Eng. Rev., 24:165-77 (2007).
Grote et al., JCat: a novel tool to adapt codon usage of a target gene to its potential expression host, Nuc. Acid. Res., 33(2):W526-31 (2005).
Haas et al., Codon usage limitation in the expression of HIV-1 envelope glycoprotein. Curr. Biol. 6: 315-24 (1996).
Hirsch et al., Little vector, big gene transduction: fragmented genome reassembly of adeno-associated virus, Mol. Ther., 18(1):6-8 (2010).
Hongzhi et al., Bioengineering of coagulation factor VIII for improved secretion, Blood, 103(9):3412-9 (2004).
International Preliminary Report on Patentability, PCT/GB2013/051551 dated Dec. 16, 2014.
International Search Report and Written Opinion of the International Searching Authority, PCT/GB2013/051551, dated Dec. 30, 2013.
International Search Report and Written Opinion, International Application No. PCT/US2014/054960, dated Dec. 22, 2014.
International Search report for PCT/US2010/041378 dated Nov. 11, 2010.
Jiang et al., Evidence of multiyear factor IX expression by AAV-mediated gene transfer to skeletal muscle in an individual with severe hemophilia B. Mol. Ther. 14: 452-5 (2006).
Lam et al., An efficient and safe herpes simplex virus type 1 amplicon vector for transcriptionally targeted therapy of human hepatocellular carcinomas, Molec. Ther., 15(6):1129-36 (2007).
Lee et al., A new potent hFIX plasmid for hemophilia B gene therapy, Pharm. Res., 21(7):1229-32 (2004).
Lu et al., Complete correction of hemophilia A with adeno-associated viral vectors containing a full-size expression cassette, Human Gene Ther., 19(6):648-54 (2008).
Malhotra et al., Antioxidants reduce endoplasmic reticulum stress and improve protein secretion. Proc. Natl. Acad. Sci. USA, 105: 18525-30 (2008).
Mcintosh et al., Therapeutic levels of FVIII following a single peripheral vein administration for rAAV vector encoding a novel human factor VIII variant, Blood, 121(17):3335-44 (2013).
Miao et al., Bioengineering of coagulation factor VIII for improved secretion. Blood, 103: 3412-9 (2004).
Miao et al., Long-term and therapeutic-level hepatic gene expression of human factor IX after naked plasmid transfer in vivo. Mol. Ther. 3: 947-57 (2000).
Muyidermans, Single domain camel antibodies: current status. J. Biotechnol. 74: 277-302 (2001).
Nathwani et al., Adenovirus-associated virus vector-mediated gene transfer in hemophilia B, N. Engl. J. Med., 365(25):2357-65 (2011).
Nathwani et al., Factors influencing in vivo transduction by recombinant adeno-associated viral vectors expressing the human factor IX cDNA. Blood, 97: 1258-65 (2001).
Nathwani et al., Long-term safety and efficacy following systemic administration of a self-complementary AAV vector encoding human FIX pseudotyped with serotype 5 and 8 capsid proteins. Mol. Ther. 19: 876-85 (2011).
Nathwani et al., Self-complementary adeno-associated virus vectors containing a novel liver-specific human factor IX expression cassette enable highly efficient transduction of murine and nonhuman primate liver. Blood, 107: 2653-61 (2006).
Okuyama et al., Liver-directed gene therapy: a retroviral vector with a complete LTR and the ApoE enhancer-alpha 1-antitrypsin promoter dramatically increases expression of human alpha 1-antitrypsin in vivo. Hum. Gene Ther. 7: 637-45 (1996).
Pipe, Functional roles of the factor VIII B domain, Haemophilia, 15(6):1187-96 (2009).
Rabinowitz et al., Cross-packaging of a single adeno-associated virus (AAV) type 2 vector genome into multiple AAV serotypes enables transduction with broad specificity. J. Virol. 76: 791-801 (2002).
Radcliffe et al., Analysis of factor VIII mediated suppression of lentiviral vector titres, Gene Ther., 15(4):289-97 (2008).
Rogers, Gene therapy for hemophilia, Front Biosci., 20:556-603 (2015).
Rutledge et al., Infectious clones and vectors derived from adeno-associated virus (AAV) serotypes other than AAV type 2. J. Virol. 72: 309-19 (1998).
Sandberg et al., Structural and functional characteristics of the B-Domain-Deleted recombinant factor VIII protein, Thromb. Haemo., 85(2):93-100 (2001).
Sarkar et al., A single adeno-associated virus (AAV)-murine factor VIII vector partially corrects the hemophilia A phenotype, J. Thromb. Haemost., 1(2):220-6 (2003).
Shachter et al., Localization of a Liver-specific enhancer in the apolipoprotein E/C-I/C-II gene locus, J. Lipid. Res. 34(10):1699-707 (1993).
Srivastava et al., Nucleotide sequence and organization of the adeno-associated virus 2 genome. J. Virol. 45: 555-64 (1983).
Wang et al., Sustained correction of bleeding disorder in hemophilia B mice by gene therapy. Proc. Natl. Acad. Sci. USA 96: 3906-10 (1999).
Ward et al., Codon optimization of human factor VIII cDNAs leads to high-level expression, Blood, 117:798-807 (2011).
Wu et al., Mutational analysis of the adeno-associated virus type 2 (AAV2) capsid gene and construction of AAV2 vectors with altered tropism. J. Virol. 74: 8635-47 (2000).
Wu et al., Optimization of Self-complementary AAV Vectors for Liver-directed Expression Results in Sustained Correction of Hemophilia B at Low Vector Dose, Molec. Ther., 16(2):280-9 (2008).
Xiao et al., Production of high-titer recombinant adeno-associated virus vectors in the absence of helper adenovirus. J. Virol. 72: 2224-32 (1998).
Xie et al., Domains of the Rat rDNA promoter must be aligned stereopecifically, Mol. Cell. Biol., 12:1266-75 (1992).
Yan et al., Inverted terminal repeat sequences are important for intermolecular recombination and circularization of adeno-associated virus genomes, J. Virol., 79(1):364-79 (2005).

* cited by examiner

SEQUENCE LISTING

```
<160> NUMBER OF SEQ ID NOS: 7

<210> SEQ ID NO 1
<211> LENGTH: 51
<212> TYPE: DNA
<213> ORGANISM: Artificial sequence
<220> FEATURE:
<223> OTHER INFORMATION: Portion of modified Factor VIII B domain
      sequence

<400> SEQUENCE: 1
gccactaatg tgtctaacaa cagcaacacc agcaatgaca gcaatgtgtc t              51

<210> SEQ ID NO 2
<211> LENGTH: 93
<212> TYPE: DNA
<213> ORGANISM: Artificial sequence
<220> FEATURE:
<223> OTHER INFORMATION: Modified Factor VIII B domain sequence

<400> SEQUENCE: 2
```

```
agcttcagcc agaatgccac taatgtgtct aacaacagca acaccagcaa tgacagcaat      60
gtgtctcccc cagtgctgaa gaggcaccag agg                                  93

<210> SEQ ID NO 3
<211> LENGTH: 4425
<212> TYPE: DNA
<213> ORGANISM: Artificial sequence
<220> FEATURE:
<223> OTHER INFORMATION: Modified Factor VIII sequence

<400> SEQUENCE: 3
atgcagattg agctgagcac ctgcttcttc ctgtgcctgc tgaggttctg cttctctgcc      60
accaggagat actacctggg ggctgtggag ctgagctggg actacatgca gtctgacctg     120
ggggagctgc ctgtggatgc caggttcccc cccagagtgc caagagcttc cccttcaac      180 acctctgtgg tgtacaagaa gaccctgttt gtggagttca ctgaccacct gttcaacatt     240
gccaagccca ggccccctg gatgggcctg ctgggcccca ccatccaggc tgaggtgtat     300
gacactgtgg tgatcaccct gaagaacatg gccagccacc ctgtgagcct gcatgctgtg     360
ggggtgagct actggaaggc ctctgagggg gctgagtatg atgaccagac cagccagagg     420
gagaaggagg atgacaaggt gttccctggg gcagccaca cctatgtgtg gcaggtgctg     480
aaggagaatg gccccatggc ctctgacccc ctgtgcctga cctacagcta cctgagccat     540
gtggacctgg tgaaggacct gaactctggc ctgattgggg ccctgctggt gtgcagggag     600
ggcagcctgg ccaaggagaa gacccagacc ctgcacaagt tcatcctgct gtttgctgtg     660
tttgatgagg gcaagagctg gcactctgaa accaagaaca gcctgatgca ggacagggat     720
gctgcctctg ccagggcctg gcccaagatg cacactgtga atggctatgt gaacaggagc     780
ctgcctggcc tgattggctg ccacaggaag tctgtgtact ggcatgtgat tggcatgggc     840
accacccctg aggtgcacag catcttcctg gagggccaca cctttcctgg tcaggaaccac     900 aggcaggcca gcctggagat cagccccatc accttcctga ctgcccagac cctgctgatg     960
gacctgggcc agttcctgct gttctgccac atcagcagcc accagcatga tggcatggag    1020
gcctatgtga aggtggacag ctgccctgag agccccagc tgaggatgaa gaacaatgag    1080
gaggctgagg actatgatga tgacctgact gactctgaga tggatgtggt gaggtttgat    1140
gatgacaaca gccccagctt catccagatc aggtctgtgg ccaagaagca ccccaagacc    1200
tgggtgcact acattgctgc tgaggaggag gactgggact atgcccccct ggtgctggcc    1260
cctgatgaca ggagctacaa gagccagtac ctgaacaatg gccccagag gattggcagg    1320 aagtacaaga aggtcaggtt catggcctac actgatgaaa ccttcaagac cagggaggcc    1380
atccagcatg agtctggcat cctgggcccc ctgctgtatg ggaggtgg ggacaccctg    1440 ctgatcatct tcaagaacca ggccagcagg ccctacaaca tctaccccca tggcatcact    1500
gatgtgaggc cctgtacag caggaggctg cccaagggg tgaagcacct gaaggacttc    1560
cccatcctgc ctgggagat cttcaagtac aagtggactg tgactgtgga ggatggcccc    1620
accaagtctg accccaggtg cctgaccaga tactacagca gctttgtgaa catggagagg    1680
gacctggcct ctgcctgat ggccccctg ctgatctgct acaaggagtc ctgtggaccag    1740 agggcaacc agatcatgtc tgacaagagg aatgtgatcc tgttctctgt gtttgatgag    1800
aacaggagct ggtacctgac tgagaacatc cagaggttcc tgcccaaccc tgctggggtg    1860
cagctggagg accctgagtt ccaggccagc aacatcatgc acagcatcaa tggctatgtg    1920
```

```
tttgacagcc tgcagctgtc tgtgtgcctg catgaggtgg cctactggta catcctgagc      1980 attgggccc agactgactt cctgtctgtg ttcttctctg gctacacctt caagcacaag       2040
atggtgtatg aggacaccct gaccctgttc cccttctctg gggagactgt gttcatgagc      2100
atggagaacc ctggcctgtg gattctgggc tgccacaact ctgacttcag gaacaggggc     2160
atgactgccc tgctgaaagt ctccagctgt gacaagaaca ctggggacta ctatgaggac     2220
agctatgagg acatctctgc ctacctgctg agcaagaaca atgccattga gcccaggagc     2280
ttcagccaga atgccactaa tgtgtctaac aacagcaaca ccagcaatga cagcaatgtg    2340
tctcccccag tgctgaagag gcaccagagg gagatcacca ggaccaccct gcagtctgac    2400
caggaggaga ttgactatga tgacaccatc tctgtggaga tgaagaagga ggactttgac   2460
atctacgacg aggacgagaa ccagagcccc aggagcttcc agaagaagac caggcactac   2520
ttcattgctg ctgtggagag gctgtgggac tatggcatga gcagcagccc ccatgtgctg    2580
aggaacaggg cccagtctgg ctctgtgccc cagttcaaga aggtggtgtt ccaggagttc    2640
actgatggca gcttcaccca gccccctgtac agaggggagc tgaatgagca cctgggcctg   2700
ctgggcccct acatcagggc tgaggtggag gacaacatca tggtgacctt caggaaccag   2760
gccagcaggc cctacagctt ctacagcagc ctgatcagct atgaggagga ccagaggcag    2820
ggggctgagc ccaggaagaa cttttgtgaag cccaatgaaa ccaagaccta cttctggaag  2880
gtgcagcacc acatggcccc caccaaggat gagtttgact gcaaggcctg gcctacttc     2940 tctgatgtgg acctggagaa ggatgtgcac tctggcctga ttggcccct gctggtgtgc    3000 cacaccaaca ccctgaaccc tgcccatggc aggcaggtga ctgtgcagga gtttgccctg   3060
ttcttcacca tctttgatga aaccaagagc tggtacttca ctgagaacat ggagaggaac   3120
tgcagggccc cctgcaacat ccagatggag gaccccacct tcaaggagaa ctacaggttc  3180
catgccatca atggctacat catggacacc ctgcctggcc tggtgatggc ccaggaccag    3240
aggatcaggt ggtacctgct gagcatgggc agcaatgaga acatccacag catccacttc   3300
tctggccatg tgttcactgt gaggaagaag gaggagtaca gatggccct gtacaacctg    3360 taccctgggg tgtttgagac tgtggagatg ctgcccagca aggctggcat ctggaggtg    3420 gagtgcctga ttggggagca cctgcatgct ggcatgagca ccctgttcct ggtgtacagc   3480
aacaagtgcc agaccccct gggcatggcc tctggccaca tcaggacatt ccagatcact   3540
gcctctggcc agtatggcca gtgggccccc aagctggcca ggctgcacta ctctggcagc   3600
atcaatgcct ggagcaccaa ggagcccttc agctggatca aggtggacct gctggccccc   3660
atgatcatcc atggcatcaa gacccagggg gccaggcaga agttcagcag cctgtacatc   3720
agccagttca tcatcatgta cagcctggat ggcaagaagt ggcagaccta cagggggcaac   3780 agcactggca ccctgatggt gttctttggc aatgtggaca gctctggcat caagcacaac   3840
atcttcaacc cccccatcat tgccagatac atcaggctgc accccacca ctacagcatc     3900 aggagcaccc tgaggatgga gctgatgggc tgtgacctga acagctgcag catgcccctg   3960
ggcatggaga gcaaggccat ctctgatgcc cagatcactg ccagcagcta cttcaccaac   4020
atgtttgcca cctggagccc cagcaaggcc aggctgcacc tgcagggcag gagcaatgcc   4080
tggaggcccc aggtcaacaa ccccaaggag tggctgcagg tggacttcca gaagaccatg   4140
aaggtgactg gggtgaccac ccaggggggtg aagagcctgc tgaccagcat gtatgtgaag   4200
gagttcctga tcagcagcag ccaggatggc accagtggaa ccctgttctt ccagaatggc   4260
aaggtgaagg tgttccaggg caaccaggac agcttcaccc ctgtggtgaa cagcctggac   4320
```

```
cccccccctgc tgaccagata cctgaggatt caccccccaga gctgggtgca ccagattgcc    4380
ctgaggatgg aggtgctggg ctgtgaggcc caggacctgt actga                     4425
```

<210> SEQ ID NO 4
<211> LENGTH: 17
<212> TYPE: PRT
<213> ORGANISM: Artificial sequence
<220> FEATURE:
<223> OTHER INFORMATION: Portion of the modified Factor VIII B domain
      sequence

<400> SEQUENCE: 4

```
Ala Thr Asn Val Ser Asn Asn Ser Asn Thr Ser Asn Asp Ser Asn Val
1               5                   10                  15

Ser
```

<210> SEQ ID NO 5
<211> LENGTH: 31
<212> TYPE: PRT
<213> ORGANISM: Artificial sequence
<220> FEATURE:
<223> OTHER INFORMATION: Modified Factor VIII B domain sequence

<400> SEQUENCE: 5

```
Ser Phe Ser Gln Asn Ala Thr Asn Val Ser Asn Asn Ser Asn Thr Ser
1               5                   10                  15

Asn Asp Ser Asn Val Ser Pro Pro Val Leu Lys Arg His Gln Arg
                20                  25                  30
```

<210> SEQ ID NO 6
<211> LENGTH: 1474
<212> TYPE: PRT
<213> ORGANISM: Artificial sequence
<220> FEATURE:
<223> OTHER INFORMATION: Modified Factor VIII sequence

<400> SEQUENCE: 6

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
                20                  25                  30

Trp Asp Tyr Met Gln Ser Asp Leu Gly Glu Leu Pro Val Asp Ala Arg
            35                  40                  45

Phe Pro Pro Arg Val Pro Lys Ser Phe Pro Phe Asn Thr Ser Val Val
        50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
                100                 105                 110

His Pro Val Ser Leu His Ala Val Gly Val Ser Tyr Trp Lys Ala Ser
            115                 120                 125

Glu Gly Ala Glu Tyr Asp Asp Gln Thr Ser Gln Arg Glu Lys Glu Asp
        130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175
```

```
Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
        260                 265                 270

Tyr Trp His Val Ile Gly Met Gly Thr Thr Pro Glu Val His Ser Ile
            275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
        340                 345                 350

Gln Leu Arg Met Lys Asn Asn Glu Glu Ala Glu Asp Tyr Asp Asp Asp
            355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
        420                 425                 430

Asn Gly Pro Gln Arg Ile Gly Arg Lys Tyr Lys Lys Val Arg Phe Met
            435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
        500                 505                 510

Gly Val Lys His Leu Lys Asp Phe Pro Ile Leu Pro Gly Glu Ile Phe
            515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
        580                 585                 590
```

-continued

```
Ile Leu Phe Ser Val Phe Asp Glu Asn Arg Ser Trp Tyr Leu Thr Glu
            595                 600                 605

Asn Ile Gln Arg Phe Leu Pro Asn Pro Ala Gly Val Gln Leu Glu Asp
        610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
                660                 665                 670

Ser Gly Tyr Thr Phe Lys His Lys Met Val Tyr Glu Asp Thr Leu Thr
            675                 680                 685

Leu Phe Pro Phe Ser Gly Glu Thr Val Phe Met Ser Met Glu Asn Pro
        690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Ala Thr Asn Val
        755                 760                 765

Ser Asn Asn Ser Asn Thr Ser Asn Asp Ser Asn Val Ser Pro Pro Val
770                 775                 780

Leu Lys Arg His Gln Arg Glu Ile Thr Arg Thr Thr Leu Gln Ser Asp
785                 790                 795                 800

Gln Glu Glu Ile Asp Tyr Asp Asp Thr Ile Ser Val Glu Met Lys Lys
                805                 810                 815

Glu Asp Phe Asp Ile Tyr Asp Glu Asp Glu Asn Gln Ser Pro Arg Ser
            820                 825                 830

Phe Gln Lys Lys Thr Arg His Tyr Phe Ile Ala Ala Val Glu Arg Leu
        835                 840                 845

Trp Asp Tyr Gly Met Ser Ser Ser Pro His Val Leu Arg Asn Arg Ala
850                 855                 860

Gln Ser Gly Ser Val Pro Gln Phe Lys Lys Val Val Phe Gln Glu Phe
865                 870                 875                 880

Thr Asp Gly Ser Phe Thr Gln Pro Leu Tyr Arg Gly Glu Leu Asn Glu
                885                 890                 895

His Leu Gly Leu Leu Gly Pro Tyr Ile Arg Ala Glu Val Glu Asp Asn
            900                 905                 910

Ile Met Val Thr Phe Arg Asn Gln Ala Ser Arg Pro Tyr Ser Phe Tyr
        915                 920                 925

Ser Ser Leu Ile Ser Tyr Glu Glu Asp Gln Arg Gln Gly Ala Glu Pro
930                 935                 940

Arg Lys Asn Phe Val Lys Pro Asn Glu Thr Lys Thr Tyr Phe Trp Lys
945                 950                 955                 960

Val Gln His His Met Ala Pro Thr Lys Asp Glu Phe Asp Cys Lys Ala
                965                 970                 975

Trp Ala Tyr Phe Ser Asp Val Asp Leu Glu Lys Asp Val His Ser Gly
            980                 985                 990

Leu Ile Gly Pro Leu Leu Val Cys  His Thr Asn Thr Leu  Asn Pro Ala
        995                 1000                1005

His Gly  Arg Gln Val Thr Val  Gln Glu Phe Ala Leu  Phe Phe Thr
```

-continued

```
                1010                1015                1020

Ile Phe Asp Glu Thr Lys Ser Trp Tyr Phe Thr Glu Asn Met Glu
    1025                1030                1035

Arg Asn Cys Arg Ala Pro Cys Asn Ile Gln Met Glu Asp Pro Thr
    1040                1045                1050

Phe Lys Glu Asn Tyr Arg Phe His Ala Ile Asn Gly Tyr Ile Met
    1055                1060                1065

Asp Thr Leu Pro Gly Leu Val Met Ala Gln Asp Gln Arg Ile Arg
    1070                1075                1080

Trp Tyr Leu Leu Ser Met Gly Ser Asn Glu Asn Ile His Ser Ile
    1085                1090                1095

His Phe Ser Gly His Val Phe Thr Val Arg Lys Lys Glu Glu Tyr
    1100                1105                1110

Lys Met Ala Leu Tyr Asn Leu Tyr Pro Gly Val Phe Glu Thr Val
    1115                1120                1125

Glu Met Leu Pro Ser Lys Ala Gly Ile Trp Arg Val Glu Cys Leu
    1130                1135                1140

Ile Gly Glu His Leu His Ala Gly Met Ser Thr Leu Phe Leu Val
    1145                1150                1155

Tyr Ser Asn Lys Cys Gln Thr Pro Leu Gly Met Ala Ser Gly His
    1160                1165                1170

Ile Arg Asp Phe Gln Ile Thr Ala Ser Gly Gln Tyr Gly Gln Trp
    1175                1180                1185

Ala Pro Lys Leu Ala Arg Leu His Tyr Ser Gly Ser Ile Asn Ala
    1190                1195                1200

Trp Ser Thr Lys Glu Pro Phe Ser Trp Ile Lys Val Asp Leu Leu
    1205                1210                1215

Ala Pro Met Ile Ile His Gly Ile Lys Thr Gln Gly Ala Arg Gln
    1220                1225                1230

Lys Phe Ser Ser Leu Tyr Ile Ser Gln Phe Ile Ile Met Tyr Ser
    1235                1240                1245

Leu Asp Gly Lys Lys Trp Gln Thr Tyr Arg Gly Asn Ser Thr Gly
    1250                1255                1260

Thr Leu Met Val Phe Phe Gly Asn Val Asp Ser Ser Gly Ile Lys
    1265                1270                1275

His Asn Ile Phe Asn Pro Pro Ile Ile Ala Arg Tyr Ile Arg Leu
    1280                1285                1290

His Pro Thr His Tyr Ser Ile Arg Ser Thr Leu Arg Met Glu Leu
    1295                1300                1305

Met Gly Cys Asp Leu Asn Ser Cys Ser Met Pro Leu Gly Met Glu
    1310                1315                1320

Ser Lys Ala Ile Ser Asp Ala Gln Ile Thr Ala Ser Ser Tyr Phe
    1325                1330                1335

Thr Asn Met Phe Ala Thr Trp Ser Pro Ser Lys Ala Arg Leu His
    1340                1345                1350

Leu Gln Gly Arg Ser Asn Ala Trp Arg Pro Gln Val Asn Asn Pro
    1355                1360                1365

Lys Glu Trp Leu Gln Val Asp Phe Gln Lys Thr Met Lys Val Thr
    1370                1375                1380

Gly Val Thr Thr Gln Gly Val Lys Ser Leu Leu Thr Ser Met Tyr
    1385                1390                1395

Val Lys Glu Phe Leu Ile Ser Ser Ser Gln Asp Gly His Gln Trp
    1400                1405                1410
```

```
Thr Leu Phe Phe Gln Asn Gly Lys Val Lys Val Phe Gln Gly Asn
    1415            1420                1425

Gln Asp Ser Phe Thr Pro Val Val Asn Ser Leu Asp Pro Pro Leu
    1430            1435                1440

Leu Thr Arg Tyr Leu Arg Ile His Pro Gln Ser Trp Val His Gln
    1445            1450                1455

Ile Ala Leu Arg Met Glu Val Leu Gly Cys Glu Ala Gln Asp Leu
    1460            1465                1470

Tyr

<210> SEQ ID NO 7
<211> LENGTH: 14
<212> TYPE: PRT
<213> ORGANISM: Artificial sequence
<220> FEATURE:
<223> OTHER INFORMATION: B domain linker sequence

<400> SEQUENCE: 7

Ser Phe Ser Gln Asn Pro Pro Val Leu Lys Arg His Gln Arg
1               5                   10
```

METHODS OF DELIVERING FACTOR VIII ENCODING NUCLEIC ACID SEQUENCES

This application is a divisional of U.S. application Ser. No. 14/407,008, now U.S. Pat. No. 9,447,168, filed Dec. 10, 2016, which is a national phase application of International Patent Application No. PCT/GB2013/51551, filed Jun. 12, 2013, which claims priority to United Kingdom Patent Application No. 1210357.8, filed Jun. 12, 2012, all of which are incorporated herein by reference in their entirety.

FIELD OF THE INVENTION

The present invention relates to a coagulation factor VIII nucleotide sequence containing a modified B domain sequence. The invention also relates to the use of this factor VIII nucleotide sequence in the treatment of haemophilia, in particular haemophilia A.

BACKGROUND TO THE INVENTION

Haemophilia A (HA) is an X-linked recessive bleeding disorder that affects approximately 1 in 5.000 males. It is caused by mutations in the coagulation factor VIII (FVIII) gene that codes for FVIII protein, an essential cofactor in the coagulation cascade. Clinical manifestations of severe FVIII deficiency are frequent unprovoked bleeding episodes, which can be life threatening and cause permanent disability. Treatment in Western countries consists of intravenous injection of plasma derived or recombinant FVIII protein concentrates at the time of a bleed, or prophylactically, to prevent bleeding episodes. The short half-life for FVIII (8-18 hours) necessitates frequent infusions, making this treatment prohibitively expensive (>£100,000/year for prophylaxis) for the majority of the world's haemophilia A patients. Chemical modification (e.g., direct conjugation of polyethylene glycol (PEG) polymers) and bioengineering of FVIII (e.g. FVIII-FAB fusion proteins) to improve the half-life of the FVIII protein show promise. However, these long acting FVIII variants do not eliminate the need for lifelong FVIII protein administration or problems of FVIII inhibitor formation which occurs in 30% of patients on standard FVIII replacement therapy.

Gene therapy, in contrast, offers the potential of a cure through continuous endogenous production of FVIII following a single administration of vector. Haemophilia A is in fact well suited for a gene replacement approach because its clinical manifestations are entirely attributable to the lack of a single gene product (FVIII) that circulates in minute amounts (200 ng/ml) in the plasma. Tightly regulated control of gene expression is not essential and a modest increase in the level of FVIII (>1% of normal) can ameliorate the severe phenotype. The consequences of gene transfer can be assessed using simple quantitative endpoints that can be easily assayed in most clinical laboratories.

Several different gene transfer strategies for FVIII replacement have been evaluated, but adeno-associated viral (AAV) vectors show the greatest promise. They have an excellent safety profile and can direct long-term transgene expression from post-mitotic tissues such as the liver. Indeed, an on-going clinical trial for gene therapy of haemophilia B has established that stable (>18 months) expression of human factor IX at levels that are sufficient for conversion of the haemophilia phenotype from severe to moderate or mild is achievable following a single peripheral vein administration of AAV vector. Several participants in this trial have been able to discontinue prophylaxis without suffering from spontaneous bleeding episodes. Similar encouraging results have emerged from clinical trials of AAV mediated gene transfer to the retina for the treatment of Leber's congenital amaurosis.

The use of AAV vectors for haemophilia A gene therapy, however, poses new challenges due to the distinct molecular and biochemical properties of human FVIII (hFVIII). When compared to other proteins of comparable size, expression of hFVIII is highly inefficient due to mRNA instability, interaction with endoplasmic reticulum (ER) chaperones, and a requirement for facilitated ER to Golgi transport through interaction with the mannose-binding lectin, LMAN1. Consequently, higher vector doses would be required to achieve therapeutic levels of hFVIII following gene transfer. Aside from increased pressure on vector production, this will increase the risk of toxicity since the potential toxicities appear to be related to the vector dose.

Bioengineering of the FVIII molecule has resulted in improvement of the FVIII expression. For instance, deletion of the FVIII B-domain, which is not required for cofactor activity, resulted in a 17-fold increase in mRNA levels over full length wild-type FVIII and a 30% increase in secreted protein (Kaufman et al, 1997; Miao et al, 2004). This has led to the development of B-domain deleted (BDD) FVIII protein concentrate, which is now widely used in the clinic. However, a significant portion of the full length FVIII and the BDD-FVIII is misfolded and retained within the endoplasmic reticulum (ER) and ultimately degraded. It has been shown that the addition of a short 226 amino-acid B-domain spacer rich in asparagine-linked oligosaccharides to BDD-hFVIII (known as N6-hFVIII) appears to further increase expression by 10 fold over that achieved with BDD-hFVIII (Cerullo et al, 2007; Miao et al, 2004). Unlike the full length and BDD-hFVIII variant, the N6-hFVIII variant does not appear to evoke an unfolded protein response (UPR) with resultant apoptosis of murine hepatocytes, thus making it a useful variant for further evaluation in the context of gene transfer (Malhotra et al, 2008).

Codon optimisation has also been used to increase expression of the FVIII protein. Codon optimised N6 (codop-hFVIII-N6) causes secretion of FVIII from cells at levels that are at least 10 fold higher than observed with wt-hFVIII-N6 (WO 2011/005968). A codon optimised version of the full length and B domain deleted FVIII have also been developed (WO 2005/0052171). Using lentiviral vectors, the in vitro potency of codon-optimised BDD-FVIII (codop-BDD-hFVIII) has been shown to be greater than wild type-BDD-FVIII. Codon optimisation of the FVIII sequence is also described in US 2010/0284971.

Another obstacle to AAV mediated gene transfer of FVIII for haemophilia A gene therapy is the size of the FVIII gene, which at 7.0 kb far exceeds the normal packaging capacity of AAV vectors. Packaging of large expression cassettes into AAV vectors has been reported but this is a highly inconsistent process that results in low yield of vector particles with reduced infectivity. AAV vectors encoding the smaller BDD-FVIII (~4.4 kb) variant under the control of a small promoter show promise. In particular, one study showed persistent expression of canine FVIII at 2.5-5% of normal over a period of 4 years in haemophilia A dogs following a single administration of rAAV encoding canine BDD-FVIII (Jiang et al, 2006). This approach has, however, not been critically assessed with human BDD-FVIII instead of its canine cognate. Another innovative approach to overcome the size constraint involves packaging the heavy (HC) and light chain (LC) cDNAs into two separate AAV vectors, taking advantage of the biochemical re-association of the HC and LC of FVIII to regenerate coagulation activity. An alternative strategy involves molecular re-association or concatemerization of the 5' and 3' regions of the large FVIII expression cassette delivered to a target cells by two separate AAV vectors (Chao et al, 2002; Chen et al, 2009). Whilst these approaches solve the packaging limitations of FVIII they create other disadvantages including the need for two AAV vectors for functional FVIII activity and risk of immunogenicity due to imbalance between expression of the LC and HC or as a result of expression of half genome sized protein product.

SUMMARY OF THE INVENTION

The present invention provides a nucleic acid molecule comprising a nucleotide sequence encoding for a functional factor VIII protein, wherein the portion of the nucleotide sequence encoding for the B domain of the factor VIII protein is between 90 and 111 base pairs (or nucleotides) in length and encodes for an amino acid sequence comprising a sequence having at least 85% identity to SEQ ID NO: 4 and which comprises six asparagine residues.

In a particular embodiment, the present invention provides a nucleic acid molecule comprising a nucleotide sequence encoding for a functional factor VIII protein, wherein the portion of the nucleotide sequence encoding for the B domain of the factor VIII protein is between 90 and 111 base pairs in length and comprises a sequence having at least 95% identity to the nucleotide sequence of SEQ ID NO: 1 and which encodes for six asparagine residues.

Preferably, the nucleotide sequence is isolated. The term "isolated" when used in relation to a nucleic acid molecule of the invention typically refers to a nucleic acid sequence that is identified and separated from at least one contaminant nucleic acid with which it is ordinarily associated in its natural source. Isolated nucleic acid may be present in a form or setting that is different from that in which it is found in nature. In contrast, non-isolated nucleic acids are nucleic acids such as DNA and RNA found in the state they exist in nature. For example, a given DNA sequence (e.g. a gene) is found on the host cell chromosome in proximity to neighbouring genes; RNA sequences, such as a specific mRNA sequence encoding a specific protein, are found in the cell as a mixture with numerous other mRNAs which encode a multitude of proteins. The isolated nucleic acid molecule of the invention may be present in single-stranded or double-stranded form. When an isolated nucleic acid molecule is to be utilized to express a protein, it will typically contain at a minimum the sense or coding strand (i.e., nucleic acid molecule may be single-stranded), but may contain both the sense and anti-sense strands (i.e., the nucleic acid molecule may be double-stranded).

The portion of the nucleotide sequence encoding for the B domain of the factor VIII protein encodes for an amino acid sequence comprising a sequence having at least 85% identity to SEQ ID NO: 4 and which comprises six asparagine residues. In some embodiments, the portion of the nucleotide sequence encoding for the B domain of the factor VIII protein encodes for an amino acid sequence comprising a sequence having at least 90% identity to SEQ ID NO: 4 and which comprises six asparagine residues. In particular embodiments, the portion of the nucleotide sequence encoding for the B domain of the factor VIII protein encodes for an amino acid sequence comprising a sequence having at least 95% identity to SEQ ID NO: 4 and which comprises six asparagine residues.

In some embodiments, the portion of the nucleotide sequence encoding for the B domain of the factor VIII protein encodes for an amino acid sequence comprising the sequence of SEQ ID NO: 4 with up to two amino acid substitutions in the amino acid residues which are not asparagine. In a preferred embodiment, there may be up to one substitution in the amino acid residues which are not asparagine.

In a preferred embodiment, the portion of the nucleotide sequence encoding for the B domain of the factor VIII protein encodes for an amino acid sequence comprising the sequence of SEQ ID NO: 4.

The portion of the nucleotide sequence encoding for the B domain of the factor VIII protein may comprise a sequence having at least 85% identity to the nucleotide sequence of SEQ ID NO: 1. The portion of the nucleotide sequence encoding for the B domain of the factor VIII protein may comprise a sequence having at least 90% identity to the nucleotide sequence of SEQ ID NO: 1. The portion of the nucleotide sequence encoding for the B domain of the factor VIII protein may comprise a sequence having at least 95% identity to the nucleotide sequence of SEQ ID NO: 1. Preferably, the portion of the nucleotide sequence encoding for the B domain of the factor VIII protein comprises a sequence having at least 96% identity to the nucleotide sequence of SEQ ID NO: 1. The portion of the nucleotide sequence encoding for the B domain of the factor VIII protein preferably comprises a sequence having at least 97%, more preferably at least 98%, more preferably still at least 99%, and even more preferably at least 99.5% identity to the nucleotide sequence of SEQ ID NO: 1. In one embodiment, the portion of the nucleotide sequence encoding for the B domain of the factor VIII protein comprises a sequence having the nucleotide sequence of SEQ ID NO: 1.

The sequence having a specified percentage identity to the nucleotide sequence of SEQ ID NO: 1 is preferably between 48 and 60 base pairs in length. Preferably, this sequence is between 48 and 57 base pairs in length. More preferably, this sequence is between 48 and 54 base pairs in length. Most preferably, this sequence is 51 base pairs in length.

The portion of the nucleotide sequence encoding for the B domain of the factor VIII protein is between 90 and 111 base pairs in length. Preferably, the portion of the nucleotide sequence encoding for the B domain of the factor VIII protein is between 90 and 108 base pairs in length. More preferably, the portion of the nucleotide sequence encoding for the B domain of the factor VIII protein is between 90 and 105, between 90 and 102, between 90 and 99, or between 90 and 96 base pairs in length. Most preferably, the portion of the nucleotide sequence encoding for the B domain of the factor VIII protein is 93 base pairs in length.

The nucleotide sequence of the invention encodes for a sequence comprising an amino acid sequence having at least 85% identity to SEQ ID NO: 4 and which comprises six asparagine residues. This amino acid sequence may be flanked on one side by a first flanking sequence and on the other side by a second flanking sequence. The first flanking sequence is a first portion of a sequence having at least 70% identity to SEQ ID NO: 7 and the second flanking sequence is a second portion of a sequence having at least 70% identity to SEQ ID NO: 7, wherein the first portion and the second portion together comprise the whole of the sequence having at least 70% identity to SEQ ID NO: 7. The first portion and the second portion may be of a sequence having at least 75% identity to SEQ ID NO: 7. In some embodiments, the first portion and the second portion may be of a sequence having at least 80% identity to SEQ ID NO: 7. The first portion and the second portion may be of a sequence having at least 85%, at least 90% or at least 95% identity to SEQ ID NO: 7. In some embodiments, the first portion and the second portion may be of SEQ ID NO: 7. For example, in one embodiment, the first flanking sequence may be the first five amino acids of SEQ ID NO: 7 and the second flanking sequence may be the last nine amino acids (i.e. the 6$^{th}$ to 14$^{th}$ amino acids) of SEQ ID NO: 7. In this way, the first and second flanking sequences together comprise the whole of SEQ ID NO: 7. In some embodiments, the first flanking sequence is between 4 and 10 amino acids in length. Likewise, the second flanking sequence may be between 4 and 10 amino acids in length. In some embodiments, the first flanking sequence is between 4 and 8 amino acids in length and the second flanking sequence is between 6 and 10 amino acids in length. In a particular embodiment, the first flanking sequence is between 4 and 6 amino acids in length and the second flanking sequence is between 8 and 10 amino acids in length. The portion of the nucleotide sequence encoding for the B domain of the factor VIII protein will encode for these flanking regions.

In a particular embodiment, the present invention provides a nucleic acid molecule comprising a nucleotide sequence encoding for a functional factor VIII protein, wherein the portion of the nucleotide sequence encoding for the B domain of the factor VIII protein is between 90 and 111 base pairs in length and comprises a sequence having at least 95% identity to the nucleotide sequence of SEQ ID NO: 1 and which encodes for six asparagine residues.

In some embodiments, the portion of the nucleotide sequence encoding for the B domain of the factor VIII protein has a sequence having at least 85% identity to the nucleotide sequence of SEQ ID NO: 2. In other embodiments, the portion of the nucleotide sequence encoding for the B domain of the factor VIII protein has a sequence having at least 90% identity to the nucleotide sequence of SEQ ID NO: 2. In further embodiments, the portion of the nucleotide sequence encoding for the B domain of the factor VIII protein has a sequence having at least 95% identity to the nucleotide sequence of SEQ ID NO: 2. The portion of the nucleotide sequence encoding for the B domain of the factor VIII protein preferably has a sequence having at least 96%, more preferably at least 97%, more preferably still at least 98%, and even more preferably at least 99% identity to the nuclcotide sequence of SEQ ID NO: 2.

In one embodiment, the portion of the nucleotide sequence encoding for the B domain of the factor VIII protein has the sequence of SEQ ID NO: 2.

The nucleic acid molecule encodes for a functional factor VIII protein, that is to say it encodes for factor VIII which, when expressed, has the functionality of wild type factor VIII. The nucleic acid molecule, when expressed in a suitable system (e.g. a host cell), produces a functional factor VIII protein and at a relatively high level. Since the factor VIII that is produced is functional, it will have a conformation which is the same as at least a portion of the wild type factor VIII. A functional factor VIII protein produced by the invention allows at least some blood coagulation to take place in a subject. This causes a decrease in the time it takes for blood to clot in a subject suffering from haemophilia, e.g. haemophilia A. Normal factor VIII participates in blood coagulation via the coagulation cascade. Normal factor VIII is a cofactor for factor IXa which, in the presence of Ca$^{+2}$ and phospholipids, forms a complex that converts factor X to the activated form Xa. Therefore, a functional factor VIII protein according to the invention can form a functional complex with factor IXa which can convert factor X to the activated form Xa.

Previously used factor VIII nucleotide sequences have had problems with expression of functional protein. This is thought to be due to inefficient expression of mRNA, protein misfolding with subsequent intracellular degradation, and inefficient transport of the primary translation product from the endoplasmic reticulum to the Golgi apparatus. The inventors have found that the nucleic acid molecule provided by the invention causes surprisingly high levels of expression of a factor VIII protein both in vitro and in vivo. This means that this nucleic acid molecule could be used in gene therapy to treat haemophilia such as haemophilia A. Further, this nucleic acid, due to its smaller size, can effectively be packaged into an AAV vector.

The domain organization of FVIII is normally made up of A1-A2-B-A3-C1-C2. As described above, the portion of the nucleotide sequence encoding for the B domain of the factor VIII protein is modified. The nucleotide sequence can have any sequence for the other domains (i.e. A1, A2, A3, C1 and C2) as long as it encodes for a functional FVIII protein. For example, the portions of the nucleotide sequence encoding for the A1, A2, A3, C1 and C2 domains of the factor VIII protein may have the wild type sequence. Alternatively, the portions of the nucleotide sequence encoding for the A1, A2, A3, C1 and C2 domains of the factor VIII protein may have a modified sequence. For example, the portions of the nucleotide sequence encoding for the A1, A2, A3, C1 and C2 domains of the factor VIII protein may have codon optimised sequences of the wild type sequence, for example, such as those disclosed in WO 2011/005968, WO 2005/0052171 or US 2010/0284971. Preferably, the portions of the nucleotide sequence encoding for the A1, A2, A3, C1 and C2 domains of the factor VIII protein have the codon optimised sequences of the codop-hFVIII-N6 sequence disclosed in WO 2011/005968. In one embodiment, the nucleic acid molecule of the invention comprises the nuclcotide sequence of SEQ ID NO: 3. In any event, the portions of the nuclcotide sequence encoding for the A1, A2, A3, C1 and C2 domains of the factor VIII protein preferably have a sequence which encodes for the wild type domains so that a functional protein is produced which is the same as the wild type protein except for the modification to the B domain.

In a particular embodiment, the nucleotide sequence encodes for a protein comprising the sequence of SEQ ID NO: 4. The portion of the nucleotide sequence encoding for the B domain of the factor VIII protein may encode for an amino acid sequence comprising the sequence of SEQ ID NO: 4.

In some embodiments, the portion of the nucleotide sequence encoding for the B domain of the factor VIII protein encodes for a sequence having at least 85% identity to the amino acid sequence of SEQ ID NO: 5. In other embodiments, the portion of the nucleotide sequence encoding for the B domain of the factor VIII protein encodes for a sequence having at least 90% identity to the amino acid sequence of SEQ ID NO: 5. In further embodiments, the portion of the nucleotide sequence encoding for the B domain of the factor VIII protein encodes for a sequence having at least 95% identity to the amino acid sequence of SEQ ID NO: 5. The portion of the nucleotide sequence encoding for the B domain of the factor VIII protein preferably encodes for a sequence having at least 96%, more preferably at least 97%, more preferably still at least 98%, and even more preferably at least 99% identity to the amino acid sequence of SEQ ID NO: 5.

In some embodiments, the portion of the nucleotide sequence encoding for the B domain of the factor VIII protein encodes for the sequence of SEQ ID NO: 5.

The sequence having a specified percentage identity to the nucleotide sequence of SEQ ID NO: 1 encodes for six asparagine residues within the B domain nucleotide sequence as a whole. Further, the sequences having identity to SEQ ID NO: 4 comprise six asparagine residues. This means that out of the 30 to 37 amino acids that are encoded for by the B domain nucleotide sequence, six of them are asparagine residues. The six asparagine residues are believed to be required for glycosylation and help the FVIII protein to be expressed. In this regard, the six asparagine residues should be positioned within the sequence so that they can be glycosylated during cellular processing. It is possible that the portion of the nucleotide sequence encoding for the B domain of the factor VIII protein may encode for more than six asparagine residues. However, the sequence having a specified percentage identity to the nucleotide sequence of SEQ ID NO: 1 should preferably encode for six asparagine residues. Likewise, the sequences having identity to SEQ ID NO: 4 should preferably encode for six asparagine residues.

It would be well with the capabilities of a skilled person to produce a nucleic acid molecule according to the invention. This could be done, for example, using chemical synthesis of a given sequence.

Further, a skilled person would readily be able to determine whether a nucleic acid according to the invention expresses a functional protein. Suitable methods would be apparent to those skilled in the art. For example, one suitable in vitro method involves inserting the nucleic acid into a vector, such as a lentiviral or an AAV vector, transducing host cells, such as 293T or HeLa cells, with the vector, and assaying for factor VIII activity. Alternatively, a suitable in vivo method involves transducing a vector containing the nucleic acid into haemophiliac mice and assaying for functional factor VIII in the plasma of the mice. Suitable methods are described in more detail below and in WO 2011/005968.

The nucleic acid can be any type of nucleic acid composed of nucleotides. The nucleic acid should be able to be expressed so that a protein is produced. Preferably, the nucleic acid is DNA or RNA.

The above description refers to the length of nucleotide sequences in base pairs, for example, between 90 and 111 base pairs in length. The term "base pair" is equivalent to the term "nucleotide" and these terms are interchangeable. Therefore, for example, the expression "between 90 and 111 base pairs in length" is equivalent to "between 90 and 111 nucleotides in length". The term "base pair" is not intended to imply that the nucleic acid molecule is double stranded, although in some embodiments, this is the case.

The present invention also provides a functional factor VIII protein, wherein the B domain of the factor VIII protein is between 30 and 37 amino acids in length, and comprises the sequence of SEQ ID NO: 4. In some embodiments, the B domain of the factor VIII protein comprises the sequence of SEQ ID NO: 5. In one embodiment, the factor VIII protein has the sequence of SEQ ID NO: 6. Some of the description above relating to the nucleic acid, in particular the parts discussing the amino acid sequence encoded by the nucleic acid, are also relevant to this aspect of the invention. Therefore, the relevant feature of the nucleic acid molecule are also intended to be features of the protein of the invention.

In a particular embodiment, there is provided a factor VIII protein encoded by the nucleic acid described above.

Also provided is a vector comprising the nucleic acid molecule of the invention. The vector may be any appropriate vector, including viral and non-viral vectors. Viral vectors include lenti-, adeno-, herpes viral vectors. The vector is preferably a recombinant adeno-associated viral (rAAV) vector or a lentiviral vector. More preferably, the vector is an rAAV vector. Alternatively, non-viral systems may be used, including using naked DNA (with or without chromatin attachment regions) or conjugated DNA that is introduced into cells by various transfection methods such as lipids or electroporation.

The vector preferably also comprises any other components required for expression of the nucleic acid molecule, such as promoters. Any appropriate promoters may be used, such as LP1, HCR-hAAT, ApoE-hAAT, and LSP. These promoters are described in more detail in the following references: LP1: Nathwani et al, 2006; HCR-hAAT: Miao et al, 2000; ApoE-hAAT: Okuyama et al, 1996; and LSP: Wang et al, 1999. A preferred promoter is also described in WO 2011/005968.

A vector according to the invention may be a gene delivery vector. Such a gene delivery vector may be a viral gene delivery vector or a non-viral gene delivery vector.

Non-viral gene delivery may be carried out using naked DNA which is the simplest method of non-viral transfection. It may be possible, for example, to administer a nucleic acid of the invention using naked plasmid DNA. Alternatively, methods such as electroporation, sonoporation or the use of a "gene gun", which shoots DNA coated gold particles into the cell using, for example, high pressure gas or an inverted .22 caliber gun, may be used.

To improve the delivery of a nucleic acid into a cell, it may be necessary to protect it from damage and its entry into the cell may be facilitated. To this end, lipoplexes and polyplexes may be used that have the ability to protect a nucleic acid from undesirable degradation during the transfection process.

Plasmid DNA may be coated with lipids in an organized structure such as a micelle or a liposome. When the organized structure is complexed with DNA it is called a lipoplex. Anionic and neutral lipids may be used for the construction of lipoplexes for synthetic vectors. Preferably, however, cationic lipids, due to their positive charge, may be used to condense negatively charged DNA molecules so as to facilitate the encapsulation of DNA into liposomes. If may be necessary to add helper lipids (usually electroneutral lipids, such as DOPE) to cationic lipids so as to form lipoplexes.

Complexes of polymers with DNA, called polyplexes, may be used to deliver a nucleic acid of the invention. Most polyplexes consist of cationic polymers and their production is regulated by ionic interactions. Polyplexes typically cannot release their DNA load into the cytoplasm. Thus, co-transfection with endosome-lytic agents (to lyse the endosome that is made during endocytosis, the process by which the polyplex enters the cell), such as inactivated adenovirus, may be necessary.

Hybrid methods may be used to deliver a nucleic acid of the invention that combines two or more techniques. Virosomes are one example; they combine liposomes with an inactivated HIV or influenza virus. Other methods involve mixing other viral vectors with cationic lipids or hybridizing viruses and may be used to deliver a nucleic acid of the invention.

A dendrimer may be used to deliver a nucleic acid of the invention, in particular, a cationic dendrimer, i.e. one with a positive surface charge. When in the presence of genetic material such as DNA or RNA, charge complimentarity leads to a temporary association of the nucleic acid with the cationic dendrimer. On reaching its destination the dendrimer-nucleic acid complex is then imported into the cell via endocytosis.

More typically, a suitable viral gene delivery vector may be used to deliver a nucleic acid of the invention. Viral vectors suitable for use in the invention may be a parvovirus, an adenovirus, a retrovirus, a lentivirus or a herpes simplex virus. The parvovirus may be an adenovirus-associated virus (AAV).

As used herein, in the context of gene delivery, the term "vector" or "gene delivery vector" may refer to a particle that functions as a gene delivery vehicle, and which comprises nucleic acid (i.e., the vector genome) packaged within, for example, an envelope or capsid. Alternatively, in some contexts, the term "vector" may be used to refer only to the vector genome.

Accordingly, the present invention provides gene delivery vectors (comprising a nucleic acid of the invention) based on animal parvoviruses, in particular dependoviruses such as infectious human or simian AAV, and the components thereof (e.g., an animal parvovirus genome) for use as vectors for introduction and/or expression of a factor VIII polypeptide in a mammalian cell. The term "parvoviral" as used herein thus encompasses dependoviruses such as any type of AAV.

Viruses of the Parvoviridae family are small DNA animal viruses. The family Parvoviridae may be divided between two subfamilies: the Parvovirinae, which infect vertebrates, and the Densovirinae, which infect insects. Members of the subfamily Parvovirinae are herein referred to as the parvoviruses and include the genus Dependovirus. As may be deduced from the name of their genus, members of the Dependovirus are unique in that they usually require coinfection with a helper virus such as adenovirus or herpes virus for productive infection in cell culture. The genus Dependovirus includes AAV, which normally infects humans (e.g., serotypes 1, 2, 3A, 3B, 4, 5, and 6) or primates (e.g., serotypes 1 and 4), and related viruses that infect other warm-blooded animals (e.g., bovine, canine, equine, and ovine adeno-associated viruses). Further information on parvoviruses and other members of the Parvoviridae is described in Kenneth I. Berns, "Parvoviridae: The Viruses and Their Replication." Chapter 69 in Fields Virology (3d Ed. 1996). For convenience the present invention is further exemplified and described herein by reference to AAV. It is, however, understood that the invention is not limited to AAV but may equally be applied to other parvoviruses.

The genomic organization of all known AAV serotypes is very similar. The genome of AAV is a linear, single-stranded DNA molecule that is less than about 5,000 nucleotides (nt) in length. Inverted terminal repeats (ITRs) flank the unique coding nucleotide sequences for the non-structural replication (Rep) proteins and the structural (VP) proteins.

The VP proteins (VP1, -2 and -3) form the capsid. The terminal 145 nt are self-complementary and are organized so that an energetically stable intramolecular duplex forming a T-shaped hairpin may be formed. These hairpin structures function as an origin for viral DNA replication, serving as primers for the cellular DNA polymerase complex. Following wild type (wt) AAV infection in mammalian cells the Rep genes (i.e. encoding Rep78 and Rep52 proteins) are expressed from the P5 promoter and the P19 promoter, respectively, and both Rep proteins have a function in the replication of the viral genome. A splicing event in the Rep ORF results in the expression of actually four Rep proteins (i.e. Rep78, Rep68, Rep52 and Rep40). However, it has been shown that the unspliced mRNA, encoding Rep78 and Rep52 proteins, in mammalian cells are sufficient for AAV vector production. Also in insect cells the Rep78 and Rep52 proteins suffice for AAV vector production.

In an AAV suitable for use as a gene therapy vector, the vector genome typically comprises a nucleic acid of the invention (as described herein) to be packaged for delivery to a target cell. According to this particular embodiment, the heterologous nucleotide sequence is located between the viral ITRs at either end of the vector genome. In further preferred embodiments, the parvovirus (e.g. AAV) cap genes and parvovirus (e.g. AAV) rep genes are deleted from the template genome (and thus from the virion DNA produced therefrom). This configuration maximizes the size of the nucleic acid sequence(s) that can be carried by the parvovirus capsid.

According to this particular embodiment, the nucleic acid of the invention is located between the viral ITRs at either end of the substrate. It is possible for a parvoviral genome to function with only one ITR. Thus, in a gene therapy vector of the invention based on a parvovirus, the vector genome is flanked by at least one ITR, but, more typically, by two AAV ITRs (generally with one either side of the vector genome, i.e. one at the 5' end and one at the 3' end). There may be intervening sequences between the nucleic acid of the invention in the vector genome and one or more of the ITRs.

Preferably, the nucleic acid encoding a functional factor VIII polypeptide (for expression in the mammalian cell) will be incorporated into a parvoviral genome located between two regular ITRs or located on either side of an ITR engineered with two D regions.

AAV sequences that may be used in the present invention for the production of AAV gene therapy vectors can be derived from the genome of any AAV serotype. Generally, the AAV serotypes have genomic sequences of significant homology at the amino acid and the nucleic acid levels, provide an identical set of genetic functions, produce virions which are essentially physically and functionally equivalent, and replicate and assemble by practically identical mechanisms. For the genomic sequence of the various AAV serotypes and an overview of the genomic similarities see e.g. GenBank Accession number U89790; GenBank Accession number J01901; GenBank Accession number AF043303; GenBank Accession number AF085716; Chiorini et al, 1997; Srivastava et al. 1983; Chiorini et al, 1999; Rutledge et al, 1998; and Wu et al, 2000. AAV serotype 1, 2, 3, 4, 5, 6, 7, 8 or 9 may be used in the present invention. However, AAV serotypes 1, 5 or 8 are preferred sources of AAV sequences for use in the context of the present invention. The sequences from the AAV serotypes may be mutated or engineered when being used in the production of gene therapy vectors.

Preferably the AAV ITR sequences for use in the context of the present invention are derived from AAV1, AAV2, AAV4 and/or AAV6. Likewise, the Rep (Rep78 and Rep52) coding sequences are preferably derived from AAV1, AAV2, AAV4 and/or AAV6. The sequences coding for the VP1, VP2, and VP3 capsid proteins for use in the context of the present invention may however be taken from any of the known 42 serotypes, more preferably from AAV1, AAV2, AAV3, AAV4, AAV5, AAV6, AAV7, AAV8 or AAV9 or newly developed AAV-like particles obtained by e.g. capsid shuffling techniques and AAV capsid libraries.

AAV Rep and ITR sequences are particularly conserved among most serotypes. The Rep78 proteins of various AAV serotypes are e.g. more than 89% identical and the total nucleotide sequence identity at the genome level between AAV2, AAV3A, AAV3B, and AAV6 is around 82% (Bantel-Schaal et al. 1999). Moreover, the Rep sequences and ITRs of many AAV serotypes are known to efficiently cross-complement (i.e., functionally substitute) corresponding sequences from other serotypes in production of AAV particles in mammalian cells. US 2003148506 reports that AAV Rep and ITR sequences also efficiently cross-complement other AAV Rep and ITR sequences in insect cells.

The AAV VP proteins are known to determine the cellular tropicity of the AAV virion. The VP protein-encoding sequences are significantly less conserved than Rep proteins and genes among different AAV serotypes. The ability of Rep and ITR sequences to cross-complement corresponding sequences of other serotypes allows for the production of pseudotyped AAV particles comprising the capsid proteins of a serotype (e.g., AAV1, 5 or 8) and the Rep and/or ITR sequences of another AAV serotype (e.g., AAV2). Such pseudotyped rAAV particles are a part of the present invention.

Modified "AAV" sequences also can be used in the context of the present invention. e.g. for the production of AAV gene therapy vectors. Such modified sequences e.g. include sequences having at least about 70%, at least about 75%, at least about 80%, at least about 85%, at least about 90%, at least about 95%, or more nucleotide and/or amino acid sequence identity (e.g., a sequence having about 75-99% nucleotide sequence identity) to an AAV1, AAV2, AAV3, AAV4, AAV5, AAV6, AAV7, AAV8 or AAV9 ITR, Rep, or VP can be used in place of wild-type AAV ITR, Rep, or VP sequences.

Although similar to other AAV serotypes in many respects, AAV5 differs from other human and simian AAV serotypes more than other known human and simian serotypes. In view thereof, the production of rAAV5 can differ from production of other serotypes in insect cells. Where methods of the invention are employed to produce rAAV5, it is preferred that one or more constructs comprising, collectively in the case of more than one construct, a nucleotide sequence comprising an AAV5 ITR, a nucleotide sequence comprises an AAV5 Rep coding sequence (i.e. a nucleotide sequence comprises an AAV5 Rep78). Such ITR and Rep sequences can be modified as desired to obtain efficient production of AAV5 or pseudotyped AAV5 vectors. For example, the start codon of the Rep sequences can be modified, VP splice sites can be modified or eliminated, and/or the VP1 start codon and nearby nucleotides can be modified to improve the production of AAV5 vectors.

Thus, the viral capsid used in the invention may be from any parvovirus, either an autonomous parvovirus or dependovirus, as described above. Preferably, the viral capsid is an AAV capsid (e.g., AAV1, AAV2, AAV3, AAV4, AAV5 or AAV6 capsid). In general, the AAV1 capsid or AAV6 capsid are preferred. The choice of parvovirus capsid may be based on a number of considerations as known in the art, e.g., the target cell type, the desired level of expression, the nature of the heterologous nucleotide sequence to be expressed, issues related to viral production, and the like. For example, the AAV1 and AAV6 capsid may be advantageously employed for skeletal muscle; AAV1, AAV5 and AAV8 for the liver and cells of the central nervous system (e.g., brain); AAV5 for cells in the airway and lung or brain; AAV3 for bone marrow cells; and AAV4 for particular cells in the brain (e.g., appendable cells).

It is within the technical skills of the skilled person to select the most appropriate virus, virus subtype or virus serotype. Some subtypes or serotypes may be more appropriate than others for a certain type of tissue.

For example, liver-specific expression of a nucleic acid of the invention may advantageously be induced by AAV-mediated transduction of liver cells. Liver is amenable to AAV-mediated transduction, and different serotypes may be used (for example, AAV1, AAV5 or AAV8). Transduction of muscle may be accomplished by administration of an AAV encoding a nucleic acid of the invention via the blood stream. Thus, intravenous or intra-arterial administration is applicable.

A parvovirus gene therapy vector prepared according to the invention may be a "hybrid" particle in which the viral TRs and viral capsid are from different parvoviruses. Preferably, the viral TRs and capsid are from different serotypes of AAV. Likewise, the parvovirus may have a "chimeric" capsid (e.g., containing sequences from different parvoviruses, preferably different AAV serotypes) or a "targeted" capsid (e.g., a directed tropism).

In the context of the invention "at least one parvoviral ITR nucleotide sequence" is understood to mean a palindromic sequence, comprising mostly complementary, symmetrically arranged sequences also referred to as "A," "B," and "C" regions. The ITR functions as an origin of replication, a site having a "cis" role in replication, i.e., being a recognition site for trans-acting replication proteins such as e.g. Rep 78 (or Rep68) which recognize the palindrome and specific sequences internal to the palindrome. One exception to the symmetry of the ITR sequence is the "D" region of the ITR. It is unique (not having a complement within one ITR). Nicking of single-stranded DNA occurs at the junction between the A and D regions. It is the region where new DNA synthesis initiates. The D region normally sits to one side of the palindrome and provides directionality to the nucleic acid replication step. A parvovirus replicating in a mammalian cell typically has two ITR sequences. It is, however, possible to engineer an ITR so that binding sites are on both strands of the A regions and D regions are located symmetrically, one on each side of the palindrome. On a double-stranded circular DNA template (e.g., a plasmid), the Rep78- or Rep68-assisted nucleic acid replication then proceeds in both directions and a single ITR suffices for parvoviral replication of a circular vector. Thus, one ITR nuclcotide sequence can be used in the context of the present invention. Preferably, however, two or another even number of regular ITRs are used. Most preferably, two ITR sequences are used. A preferred parvoviral ITR is an AAV ITR. For safety reasons it may be desirable to construct a parvoviral (AAV) vector that is unable to further propagate after initial introduction into a cell. Such a safety mechanism for limiting undesirable vector propagation in a recipient may be provided by using AAV with a chimeric ITR as described in US 2003148506.

Those skilled in the art will appreciate that the viral Rep protein(s) used for producing an AAV vector of the invention may be selected with consideration for the source of the viral ITRs. For example, the AAV5 ITR typically interacts more efficiently with the AAV5 Rep protein, although it is not necessary that the serotype of ITR and Rep protein(s) are matched.

The ITR(s) used in the invention are typically functional, i.e. they may be fully resolvable and are preferably AAV sequences, with serotypes 1, 2, 3, 4, 5 or 6 being preferred. Resolvable AAV ITRs according to the present invention need not have a wild-type ITR sequence (e.g., a wild-type sequence may be altered by insertion, deletion, truncation or missense mutations), as long as the ITR mediates the desired functions, e.g., virus packaging, integration, and/or provirus rescue, and the like.

Advantageously, by using a gene therapy vector as compared with previous approaches, the restoration of protein synthesis, i.e. factor VIII synthesis, is a characteristic that the transduced cells acquire permanently or for a sustained period of time, thus avoiding the need for continuous administration to achieve a therapeutic effect.

Accordingly, the vectors of the invention therefore represent a tool for the development of strategies for the in vivo delivery of a nucleic acid of the invention, by engineering the nucleic acid within a gene therapy vector that efficiently transduces an appropriate cell type, such as a liver cell.

In a further aspect of the invention, a host is provided comprising the vector described above. Preferably, the vector is capable of expressing the nucleic acid molecule of the invention in the host. The host may be any suitable host.

As used herein, the term "host" refers to organisms and/or cells which harbour a nucleic acid molecule or a vector of the invention, as well as organisms and/or cells that are suitable for use in expressing a recombinant gene or protein. It is not intended that the present invention be limited to any particular type of cell or organism. Indeed, it is contemplated that any suitable organism and/or cell will find use in the present invention as a host. A host cell may be in the form of a single cell, a population of similar or different cells, for example in the form of a culture (such as a liquid culture or a culture on a solid substrate), an organism or part thereof.

A host cell according to the invention may permit the expression of a nucleic acid molecule of the invention. Thus, the host cell may be, for example, a bacterial, a yeast, an insect or a mammalian cell.

Any insect cell which allows for replication of a recombinant parvoviral (rAAV) vector and which can be maintained in culture can be used in accordance with the present invention. For example, the cell line used can be from *Spodoptera frugiperda, drosophila* cell lines, or mosquito cell lines. e.g., *Aedesalbopictus* derived cell lines. Preferred insect cells or cell lines are cells from the insect species which are susceptible to baculovirus infection, including e.g. Se301, SeIZD2109, SeUCR1, Sf9, Sf900+, Sf21, BTI-TN-5B1-4, MG-1, Tn368, HzAm1, Ha2302, Hz2E5, High Five (Invitrogen, CA, USA) and expresSF+® (U.S. Pat. No. 6,103,526; Protein Sciences Corp., CT, USA).

In addition, the invention provides a method for the preparation of a parvoviral gene delivery vector, the method comprising the steps of:

(a) providing an insect cell comprising one or more nucleic acid constructs comprising:
  (i) a nucleic acid molecule of the invention that is flanked by at least one parvoviral inverted terminal repeat nucleotide sequence;
  (ii) a first expression cassette comprising a nucleotide sequence encoding one or more parvoviral Rep proteins which is operably linked to a promoter that is capable of driving expression of the Rep protein(s) in the insect cell;
  (iii) a second expression cassette comprising a nucleotide sequence encoding one or more parvoviral capsid proteins which is operably linked to a promoter that is capable of driving expression of the capsid protein(s) in the insect cell;

(b) culturing the insect cell defined in (a) under conditions conducive to the expression of the Rep and the capsid proteins; and, optionally, (c) recovering the parvoviral gene delivery vector.

In general, therefore, the method of the invention allows the production of a parvoviral gene delivery vector (comprising a nucleic acid of the invention) in an insect cell. Preferably, the method comprises the steps of: (a) culturing an insect cell as defined above under conditions such that the parvoviral (e.g. AAV) vector is produced; and, (b) recovering the recombinant parvoviral (e.g. AAV) vector. Preferably, the parvoviral gene delivery vector is an AAV gene delivery vector.

It is understood here that the (AAV) vector produced in such a method preferably is an infectious parvoviral or AAV virion that comprises a parvoviral genome, which itself comprises a nucleic acid of the invention. Growing conditions for insect cells in culture, and production of heterologous products in insect cells in culture are well-known in the art and described e.g. in the above cited references on molecular engineering of insects cells.

In a method of the invention, a nucleic acid of the invention that is flanked by at least one parvoviral ITR sequence is provided. This type of sequence is described in detail above. Preferably, the nucleic acid of the invention is sequence is located between two parvoviral ITR sequences.

The first expression cassette comprises a nucleotide sequence encoding one or more parvoviral Rep proteins which is operably linked to a first promoter that is capable of driving expression of the Rep protein(s) in the insect cell.

A nucleotide sequence encoding animal parvoviruses Rep proteins is herein understood as a nucleotide sequence encoding the non-structural Rep proteins that are required and sufficient for parvoviral vector production in insect cells such the Rep78 and Rep52 proteins, or the Rep68 and Rep40 proteins, or the combination of two or more thereof.

The animal parvovirus nucleotide sequence preferably is from a dependovirus, more preferably from a human or simian adeno-associated virus (AAV) and most preferably from an AAV which normally infects humans (e.g., serotypes 1, 2, 3A, 3B, 4, 5, and 6) or primates (e.g., serotypes 1 and 4). Rep coding sequences are well known to those skilled in the art and suitable sequences are referred to and described in detail in WO2007/148971 and also in WO2009/014445.

Preferably, the nucleotide sequence encodes animal parvoviruses Rep proteins that are required and sufficient for parvoviral vector production in insect cells.

The second expression cassette comprises a nucleotide sequence encoding one or more parvoviral capsid proteins which is operably linked to a promoter that is capable of driving expression of the capsid protein(s) in the insect cell. The capsid protein(s) expressed may be one or more of those described above.

Preferably, the nucleotide sequence encodes animal parvoviruses cap proteins that are required and sufficient for parvoviral vector production in insect cells.

These three sequences (genome, rep encoding and cap encoding) are provided in an insect cell by way of one or more nucleic acid constructs, for example one, two or three nucleic acid constructs. Preferably then, the one or nucleic acid constructs for the vector genome and expression of the parvoviral Rep and cap proteins in insect cells is an insect cell-compatible vector. An "insect cell-compatible vector" or "vector" is understood to a nucleic acid molecule capable of productive transformation or transfection of an insect or insect cell. Exemplary biological vectors include plasmids, linear nucleic acid molecules, and recombinant viruses. Any vector can be employed as long as it is insect cell-compatible. The vector may integrate into the insect cells genome but the presence of the vector in the insect cell need not be permanent and transient episomal vectors are also included. The vectors can be introduced by any means known, for example by chemical treatment of the cells, electroporation, or infection. In a preferred embodiment, the vector is a baculovirus, a viral vector, or a plasmid. In a more preferred embodiment, the vector is a baculovirus, i.e. the construct is a baculoviral vector. Baculoviral vectors and methods for their use are well known to those skilled in the art.

Typically then, a method of the invention for producing a parvoviral gene delivery vector comprises: providing to a cell permissive for parvovirus replication (a) a nucleotide sequence encoding a template for producing vector genome of the invention (as described in detail herein); (b) nucleotide sequences sufficient for replication of the template to produce a vector genome (the first expression cassette defined above); (c) nucleotide sequences sufficient to package the vector genome into a parvovirus capsid (the second expression cassette defined above), under conditions sufficient for replication and packaging of the vector genome into the parvovirus capsid, whereby parvovirus particles comprising the vector genome encapsidated within the parvovirus capsid are produced in the cell. Preferably, the parvovirus replication and/or capsid coding sequences are AAV sequences.

A method of the invention may preferably comprise the step of affinity-purification of the (virions comprising the) recombinant parvoviral (rAAV) vector using an anti-AAV antibody, preferably an immobilised antibody. The anti-AAV antibody preferably is a monoclonal antibody. A particularly suitable antibody is a single chain camelid antibody or a fragment thereof as e.g. obtainable from camels or llamas (see e.g. Muyldermans, 2001). The antibody for affinity-purification of rAAV preferably is an antibody that specifically binds an epitope on a AAV capsid protein, whereby preferably the epitope is an epitope that is present on capsid protein of more than one AAV serotype. E.g. the antibody may be raised or selected on the basis of specific binding to AAV2 capsid but at the same time also it may also specifically bind to AAV1, AAV3, AAV5, AAV6, AAV8 or AAV9 capsids.

The invention also provides a means for delivering a nucleic acid of the invention into a broad range of cells, including dividing and non-dividing cells. The present invention may be employed to deliver a nucleic acid of the invention to a cell in vitro, e.g. to produce a polypeptide encoded by such a nucleic acid molecule in vitro or for ex vivo gene therapy.

The nucleic acid molecule, vector, cells and methods/use of the present invention are additionally useful in a method of delivering a nucleic acid of the invention to a host in need thereof, typically a host suffering from haemophilia such as haemophilia A.

The present invention finds use in both veterinary and medical applications. Suitable subjects for gene delivery methods as described herein include both avians and mammals, with mammals being preferred. The term "avian" as used herein includes, but is not limited to, chickens, ducks, geese, quail, turkeys and pheasants. The term "mammal" as used herein includes, but is not limited to, humans, bovines, ovines, caprines, equines, felines, canines, lagomorphs, etc. Human subjects are most preferred. Human subjects include foetuses, neonates, infants, juveniles, and adults.

The invention thus provides a pharmaceutical composition comprising a nucleic acid or a vector of the invention and a pharmaceutically acceptable carrier or diluent and/or other medicinal agent, pharmaceutical agent or adjuvant, etc.

For injection, the carrier will typically be a liquid. For other methods of administration, the carrier may be either solid or liquid. For inhalation administration, the carrier will be respirable, and will preferably be in solid or liquid particulate form. As an injection medium, it is preferred to use water that contains the additives usual for injection solutions, such as stabilizing agents, salts or saline, and/or buffers.

In general, a "pharmaceutically acceptable carrier" is one that is not toxic or unduly detrimental to cells. Exemplary pharmaceutically acceptable carriers include sterile, pyrogen-free water and sterile, pyrogen-free, phosphate buffered saline. Pharmaceutically acceptable carriers include physiologically acceptable carriers. The term "pharmaceutically acceptable carrier" includes any and all solvents, dispersion media, coatings, antibacterial and antifungal agents, isotonic and absorption delaying agents, and the like that are physiologically compatible.

By "pharmaceutically acceptable" it is meant a material that is not biologically or otherwise undesirable, i.e., the material may be administered to a subject without causing any undesirable biological effects. Thus, such a pharmaceutical composition may be used, for example, in transfection of a cell ex vivo or in administering a viral particle or cell directly to a subject.

A carrier may be suitable for parenteral administration, which includes intravenous, intraperitoneal or intramuscular administration. Alternatively, the carrier may be suitable for sublingual or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated.

Pharmaceutical compositions are typically sterile and stable under the conditions of manufacture and storage. Pharmaceutical compositions may be formulated as a solution, microemulsion, liposome, or other ordered structure suitable to accommodate high drug concentration. The carrier may be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. A nucleic acid or vector of the invention may be administered in a time or controlled release formulation, for example in a composition which includes a slow release polymer or other carriers that will protect the compound against rapid release, including implants and microencapsulated delivery systems. Biodegradable, biocompatible polymers may for example be used, such as ethylene vinyl acetate, polyanhydrides, polyglycolic acid, collagen, polyorthoesters, polylactic acid and polylactic, polyglycolic copolymers (PLG).

The parvoviral, for example AAV, vector of the invention may be of use in transferring genetic material to a cell. Such transfer may take place in vitro, ex vivo or in vivo.

Accordingly, the invention provides a method for delivering a nucleotide sequence to a cell, which method comprises contacting a nucleic acid, a vector, or a pharmaceutical composition as described herein under conditions such the nucleic acid or vector of the invention enters the cell. The cell may be a cell in vitro, ex vivo or in vivo.

The invention also provides a method of treating haemophilia comprising administering an effective amount of a nucleic acid, a protein or a vector according to the invention to a patient suffering from haemophilia. Preferably the patient is suffering from haemophilia A. Preferably, the patient is human.

When haemophilia, e.g. haemophilia A, is "treated" in the above method, this means that one or more symptoms of haemophilia are ameliorated. It does not mean that the symptoms of haemophilia are completely remedied so that they are no longer present in the patient, although in some methods, this may be the case. The method of treating results in one or more of the symptoms of haemophilia, e.g. haemophilia A, being less severe than before treatment.

Further, the invention also provides a method for delivering or administering a nucleotide sequence to a subject, which method comprises administering to the said subject a nucleic acid, a vector, or a pharmaceutical composition as described herein. In particular, the present invention provides a method of administering a nucleic acid molecule of the invention to a subject, comprising administering to the subject a parvoviral gene therapy vector according to the invention, optionally together with a pharmaceutically acceptable carrier. Preferably, the parvoviral gene therapy vector is administered in a therapeutically-effective amount to a subject in need thereof. That is to say, administration according to the invention is typically carried out under conditions that result in the expression of functional factor VIII at a level that provides a therapeutic effect in a subject in need thereof.

Delivery of a nucleic acid or vector of the invention to a host cell in vivo may result in an increase of functional factor VIII in the host, for example to a level that ameliorates one or more symptoms of a blood clotting disorder such as haemophilia A.

The level of naturally occurring factor VIII in a subject suffering from haemophilia A varies depending on the severity of the haemophilia. Patients with a severe form of the disease have factor VIII levels of less than about 1% of the level found in a normal healthy subject (referred to herein as "a normal level". A normal level is about 50-150 IU/dL). Patients with a moderate form of the disease have factor VIII levels of between about 1% and about 5% of a normal level. Patients with a mild form of the disease have factor VIII levels of more than about 5% of a normal level; typically between about 5% and about 30% of a normal level.

It has been found that when the method of treatment of the invention is used, it can cause an increase in the level of functional factor VIII of at least about 1% of normal levels, i.e. in addition to the factor VIII level present in the subject before treatment. In a subject suffering from haemophilia A, such an increase can cause amelioration of a symptom of haemophilia. In particular, an increase of at least 1% can reduce the frequency of bleeding that occurs in sufferers of haemophilia A, especially those with a severe form of the disease. In one embodiment, the method of treatment causes an increase in the level of functional factor VIII of at least about 5% of normal levels. This could change the phenotype of the disease from severe to mild. Patients with a mild form of the disease rarely have spontaneous bleeding. In other embodiments, the method of treatment of the invention causes an increase in the level of functional factor VIII of at least about 2%, at least about 3%, at least about 4%, at least about 10%, at least about 15%, at least about 20% or at least about 25% of normal levels. In a particular embodiment, the method of treatment of the invention causes an increase in the level of functional factor VIII of at least about 30% of normal levels. This level of increase would virtually normalise coagulation of blood in subjects suffering haemophilia A. Such subjects are unlikely to require factor VIII concentrates following trauma or during surgery.

In another embodiment, the method of treatment of the invention may cause an increase in the level of functional factor VIII to at least about 1% of normal levels. The method of treatment may cause an increase in the level of functional factor VIII to at least about 5% of normal levels. In other embodiments, the method of treatment of the invention may cause an increase in the level of functional factor VIII to at least about 2%, at least about 3%, at least about 4%, at least about 10%, at least about 15%, at least about 20% or at least about 25% of normal levels. In a particular embodiment, the method of treatment of the invention causes an increase in the level of functional factor VIII to at least about 30% of normal levels. A subject whose functional factor VIII level has been increase to 30% or more will have virtually normal coagulation of blood.

In one embodiment, the method of treatment of the invention causes an increase in the level of functional factor VIII to, at most, normal levels.

The level of functional factor VIII can be measured relatively easily and methods for measuring factor VIII levels are well known to those skilled in the art. Many clotting assays are available, including chromogenic and clotting based assays. ELISA tests are also widely available. A particular method is to measure the level of factor VIII:C, which is a lab measure of the clotting activity of factor VIII. A normal level of factor VIII:C is 46.8 to 141.8 IU/dL or 0.468-1.4 IU/ml.

A further method is to measure the activated partial thromboplastin time (aPTT) which is a measure of the ability of blood to clot. A normal aPTT is between about 24 and about 34 seconds. A subject suffering from haemophilia, e.g. haemophilia A, will have a longer aPTT. This method can be used in combination with prothrombin time measurement.

Also provided is a nucleic acid molecule, protein or vector of the invention for use in therapy, especially in the treatment of haemophilia, particularly haemophilia A.

The use of a nucleic acid molecule, protein or vector of the invention in the manufacture of a medicament for the treatment of haemophilia, particularly haemophilia A, is also provided.

The invention also provides a nucleic acid or a vector of the invention for use in the treatment of the human or animal body by therapy. In particular, a nucleic acid or a vector of the invention is provided for use in the treatment of a blood clotting disorder such as haemophilia, for example haemophilia A. A nucleic acid or a vector of the invention is provided for use in ameliorating one or more symptoms of a blood clotting disorder, for example by reducing the frequency and/or severity of bleeding episodes.

The invention further provides a method of treatment of a blood clotting disorder, which method comprises the step of administering an effective amount of a nucleic acid or a vector of the invention to a subject in need thereof.

Accordingly, the invention further provides use of a nucleic acid or vector as described herein in the manufacture of a medicament for use in the administration of a nucleic acid to a subject. Further, the invention provides a nucleic acid or vector as described herein in the manufacture of a medicament for use in the treatment of a blood clotting disorder.

Typically, a nucleic acid or a vector of the invention may be administered to a subject by gene therapy, in particular by use of a parvoviral gene therapy vector such as AAV. General methods for gene therapy are known in the art. The vector, composition or pharmaceutical composition may be delivered to a cell in vitro or ex vivo or to a subject in vivo by any suitable method known in the art. Alternatively, the vector may be delivered to a cell ex vivo, and the cell administered to a subject, as known in the art. In general, the present invention can be employed to deliver any nucleic acid of the invention to a cell in vitro, ex vivo, or in vivo.

The present invention further provides a method of delivering a nucleic acid to a cell. Typically, for in vitro methods, the virus may be introduced into the cell by standard viral transduction methods, as are known in the art.

Preferably, the virus particles are added to the cells at the appropriate multiplicity of infection according to standard transduction methods appropriate for the particular target cells. Titres of virus to administer can vary, depending upon the target cell type and the particular virus vector, and may be determined by those of skill in the art without undue experimentation.

Cells may be removed from a subject, the parvovirus vector is introduced therein, and the cells are then replaced back into the subject. Methods of removing cells from subject for treatment ex vivo, followed by introduction back into the subject are known in the art.

Alternatively, an AAV vector may be introduced into cells from another subject, into cultured cells, or into cells from any other suitable source, and the cells are administered to a subject in need thereof.

A further aspect of the invention is a method of treating subjects in vivo with a nucleic acid or vector of the invention. Administration of a nucleic acid or vector of the present invention to a human subject or an animal in need thereof can be by any means known in the art for administering virus vectors.

A nucleic acid or vector of the invention will typically be included in a pharmaceutical composition as set out above. Such compositions include the nucleic acid or vector in an effective amount, sufficient to provide a desired therapeutic or prophylactic effect, and a pharmaceutically acceptable carrier or excipient. An "effective amount" includes a therapeutically effective amount or a prophylactically effective amount.

A "therapeutically effective amount" refers to an amount effective, at dosages and for periods of time necessary, to achieve the desired therapeutic result, such as raising the level of functional factor VIII in a subject (so as to lead to functional factor VIII production to a level sufficient to ameliorate the symptoms of the disease associated with a lack of that protein).

A therapeutically effective amount of a nucleic acid molecule or vector of the invention may vary according to factors such as the disease state, age, sex, and weight of the individual, and the ability of the nucleic acid molecule or vector to elicit a desired response in the individual. Dosage regimens may be adjusted to provide the optimum therapeutic response. A therapeutically effective amount is also typically one in which any toxic or detrimental effects of the nucleic acid molecule or vector are outweighed by the therapeutically beneficial effects.

Viral gene therapy vectors may be administered to a cell or host in a biologically-effective amount. A "biologically-effective" amount of the virus vector is an amount that is sufficient to result in infection (or transduction) and expression of the heterologous nucleic acid sequence in the cell. If the virus is administered to a cell in vivo (e.g., the virus is administered to a subject), a "biologically-effective" amount of the virus vector is an amount that is sufficient to result in transduction and expression of a nucleic acid according to the invention in a target cell.

For a nucleic acid molecule or vector of the invention, such as a gene therapy vector, the dosage to be administered may depend to a large extent on the condition and size of the subject being treated as well as the therapeutic formulation, frequency of treatment and the route of administration. Regimens for continuing therapy, including dose, formulation, and frequency may be guided by the initial response and clinical judgment. The parenteral route of injection into the interstitial space of tissue may be preferred, although other parenteral routes, such as inhalation of an aerosol formulation, may be required in specific administration. In some protocols, a formulation comprising the gene and gene delivery system in an aqueous carrier is injected into tissue in appropriate amounts.

Exemplary modes of administration include oral, rectal, transmucosal, topical, transdermal, inhalation, parenteral (e.g., intravenous, subcutaneous, intradermal, intramuscular, and intraarticular) administration, and the like, as well as direct tissue or organ injection, alternatively, intrathecal, direct intramuscular, intraventricular, intravenous, intraperitoneal, intranasal, or intraocular injections. Injectables can be prepared in conventional forms, either as liquid solutions or suspensions, solid forms suitable for solution or suspension in liquid prior to injection, or as emulsions. Alternatively, one may administer the virus in a local rather than systemic manner, for example, in a depot or sustained-release formulation.

The tissue/cell type to be administered a nucleic acid molecule or vector of the invention may be of any type, but will typically be a hepatic/liver cell. It is not intended that the present invention be limited to any particular route of administration. However, in order that liver cells are transduced, a nucleic acid molecule or vector of the present invention may successfully be administered via the portal or arterial vasculature. Alternatively, the cell may be any progenitor cell. As a further alternative, the cell can be a stem cell (e.g., a liver stem cell). The tissue target may be specific or it may be a combination of several tissues, for example the liver and muscle tissues.

In the case of a gene therapy vector, the effective dose range for small animals such as mice, following intramuscular injection, may be between about $1\times10^{11}$ and about $1\times10^{12}$ genome copy (gc)/kg, and for larger animals (cats) and possibly human subjects, between about $1\times10^{10}$ and about $1\times10^{13}$ gc/kg. Dosages of the parvovirus gene therapy vector of the invention will depend upon the mode of administration, the disease or condition to be treated, the individual subject's condition, the particular virus vector, and the gene to be delivered, and can be determined in a routine manner. Typically, an amount of about $10^3$ to about $10^{16}$ virus particles per dose may be suitable. Preferably, an amount of about $10^9$ to about $10^{14}$ virus particles per dose is used. When treated in this way, a subject may receive a single dose of virus particles so that the viral particles effect treatment in a single administration.

The amount of active compound in the compositions of the invention may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation.

It may be advantageous to formulate parenteral compositions in dosage unit form for ease of administration and uniformity of dosage. "Dosage unit form" as used herein refers to physically discrete units suited as unitary dosages for subjects to be treated; each unit containing a predetermined quantity of active compound calculated to produce the desired therapeutic effect in association with the required pharmaceutical carrier. The specification for the dosage unit forms of the invention may be dictated by the unique characteristics of the active compound and the particular therapeutic effect to be achieved, and by the limitations inherent in the art of compounding such an active compound for the treatment of a condition in individuals.

Many methods for the preparation of such formulations are patented or generally known to those skilled in the art.

Also provided is a FVIII protein or glycoprotein expressed by a host cell of the invention.

Further provided is a transgenic animal comprising cells comprising a vector according to the invention. Preferably the animal is a non-human mammal, especially a primate such as a macaque. Alternatively, the animal may be a rodent, especially a mouse; or may be canine, feline, ovine or porcine.

In the description above, the term "identity" is used to refer to the similarity of two sequences. For the purpose of this invention, it is defined here that in order to determine the percent identity of two nucleic acid sequences, the sequences are aligned for optimal comparison purposes (e.g., gaps can be introduced in the sequence of a first nucleic acid for optimal alignment with a second amino or nucleic acid sequence). The nucleotide residues at nucleotide positions are then compared. When a position in the first sequence is occupied by the same amino acid or nucleotide residue as the corresponding position in the second sequence, then the molecules are identical at that position. The percent identity between the two sequences is a function of the number of identical positions shared by the sequences (i.e., % identity=number of identical positions/total number of positions (i.e. overlapping positions)×100). Preferably, the two sequences are the same length.

A sequence comparison may be carried out over the entire lengths of the two sequences being compared or over fragment of the two sequences. Typically, the comparison will be carried out over the full length of the two sequences being compared. However, sequence identity may be carried out over a region of, for example, about twenty, about fifty, about one hundred, about two hundred, about five hundred, about 1000, about 2000, about 3000, about 4000, about 4500, about 5000 or more contiguous nucleic acid residues.

The skilled person will be aware of the fact that several different computer programs are available to determine the homology between two sequences. For instance, a comparison of sequences and determination of percent identity between two sequences can be accomplished using a mathematical algorithm. In a preferred embodiment, the percent identity between two amino acid or nucleic acid sequences is determined using the Needleman and Wunsch (1970) algorithm which has been incorporated into the GAP program in the Accelrys GCG software package (available at www.accelrys.com/products/gcg/), using either a Blosum 62 matrix or a PAM250 matrix, and a gap weight of 16, 14, 12, 10, 8, 6, or 4 and a length weight of 1, 2, 3, 4, 5, or 6. The skilled person will appreciate that all these different parameters will yield slightly different results but that the overall percentage identity of two sequences is not significantly altered when using different algorithms.

The nucleic acid sequences of the present invention can further be used as a "query sequence" to perform a search against public databases to, for example, identify other family members or related sequences. Such searches can be performed using the BLASTN and BLASTP programs (version 2.0) of Altschul. et al. 1990. BLAST protein searches can be performed with the BLASTP program, score=50, wordlength=3 to obtain amino acid sequences homologous to protein molecules of the invention. To obtain gapped alignments for comparison purposes, Gapped BLAST can be utilized as described in Altschul et al, 1997. When utilizing BLAST and Gapped BLAST programs, the default parameters of the respective programs (e.g., BLASTP and BLASTN) can be used. See the homepage of the National Center for Biotechnology Information at www.ncbi.nlm.nih.gov.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety.

A skilled person will appreciate that all aspects of the invention, whether they relate to, for example, the nucleic acid, the vector, the host cell or the use, are equally applicable to all other aspects of the invention. In particular, aspects of the method of treatment, for example, the administration of the nucleic acid or vector, may have been described in greater detail than in some of the other aspects of the invention, for example, relating to the use of the nucleic acid or vector for treating haemophilia, e.g. haemophilia A. However, the skilled person will appreciate where more detailed information has been given for a particular aspect of the invention, this information is likely to be equally applicable to other aspects of the invention. Further, the skilled person will also appreciate that the description relating to the method of treatment is equally applicable to the use of the nucleic acid or vector in treating haemophilia, e.g. haemophilia A.

The invention will now be described in detail, by way of example only, with reference to the drawings in which:

DETAILED DESCRIPTION OF THE INVENTION

Figure 1:
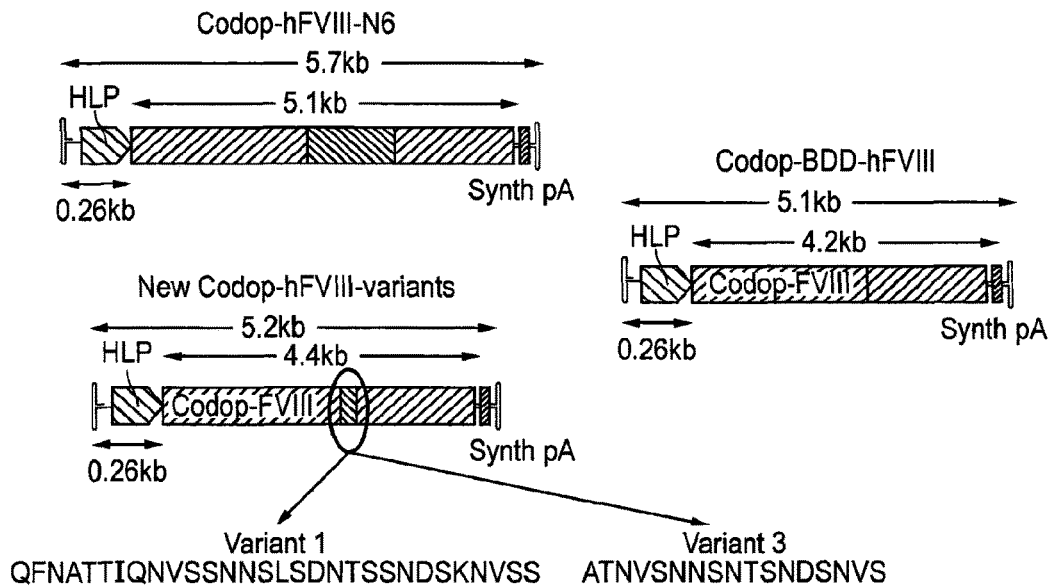
FIG. 1 is a schematic of rAAV plasmids encoding codon optimised hFVIII-N6 (top panel), codon optimised B domain deleted form (right central panel) and hFVIII variants (bottom panel) containing the 6 asparagine moieties (in bold) that are thought to be required for glycosylation. The B domain is in the middle of the constructs shown in lighter grey. In addition, to the FVIII cDNA, the expression cassette also contains a smaller HLP promoter and a synthetic polyadenylation (Synth pA) signal. The size of the FVIII cDNA as well as the whole rAAV expression cassette is also shown. The full sequence of the B domain of the hFVIII variants (variants 1 and 3) also has a 14 amino acid sequence which flanks the sequences shown for each variant. In addition, the B domain deleted form has the same 14 amino acid sequence which acts as a linker between the domains on either side (the A2 and A3 domains).

In order to develop a safe and efficient gene transfer strategy for the treatment of haemophilia A (HA), the most common inherited bleeding disorder, the inventors have developed a new FVIII variant called codop-hFVIII-V3 (FIG. 1). This variant builds on a previous variant, a 5013 bp codon-optimised FVIII called codop-hFVIII-N6. The inventors have further modified codop-hFVIII-N6 to improve the efficiency with which it is packaged into rAAV without compromising its potency in vivo.

The cDNA in codop-hFVIII-V3 has been modified to reduce its size to 4424 bp (FIG. 1) through the replacement of the 678 bp B domain spacer sequence with a 93 bp linker that codes for 31 amino acids of which 17 amino acids are unique, including the 6 asparagine moieties believed to be required for efficient cellular processing of FVIII.

Figure 2:
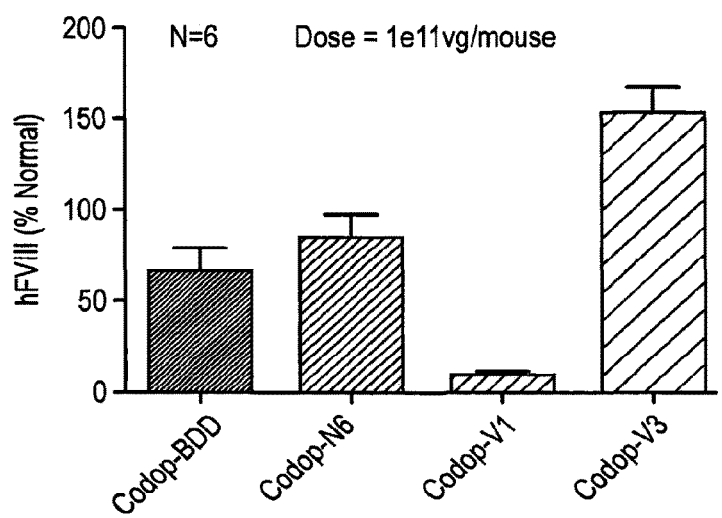
FIG. 2 shows the mean hFVIII levels±SEM in murine plasma after a single tail vein administration of rAAV-hFVIII constructs pseudotyped with serotype 8 capsid (dose=$1\times10^{11}$ vg/mouse, N=6/group).
Figure 3:
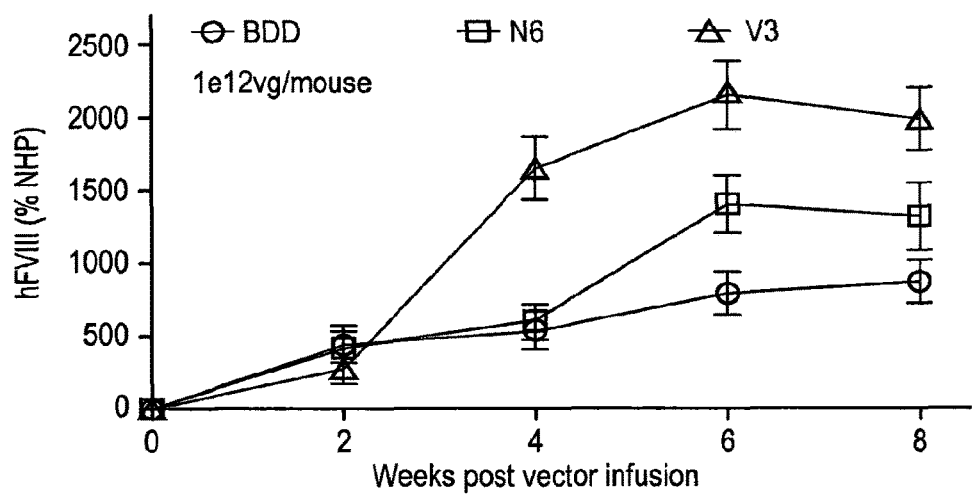
FIG. 3 shows FVIII activity level in F8−/− mice following a single tail vein administration of high dose of rAAV-HLP-codop-hFVIII vectors (dose=$1\times10^{12}$ vg/mouse, N=5/6 animals/group).

The context in which these 6 asparagine moieties are brought together is important, rAAV vectors encoding codop-hFVIII-V1 mediated FVIII expression that was 16 and 10 fold lower than vectors encoding codop-hFVIII-V3 and codop-hFVIII-N6, respectively, in cohorts of mice after a single tail vein injection of $1\times10^{11}$ vector genomes (vg)/mouse (FIG. 2). This difference was highly significant (p=0.0015). Importantly, both codop-hFVIII-V3 and codop-hFVIII-N6 mediated significantly higher level of expression than codop-BDD-hFVIII (FIG. 3).

Figure 4:
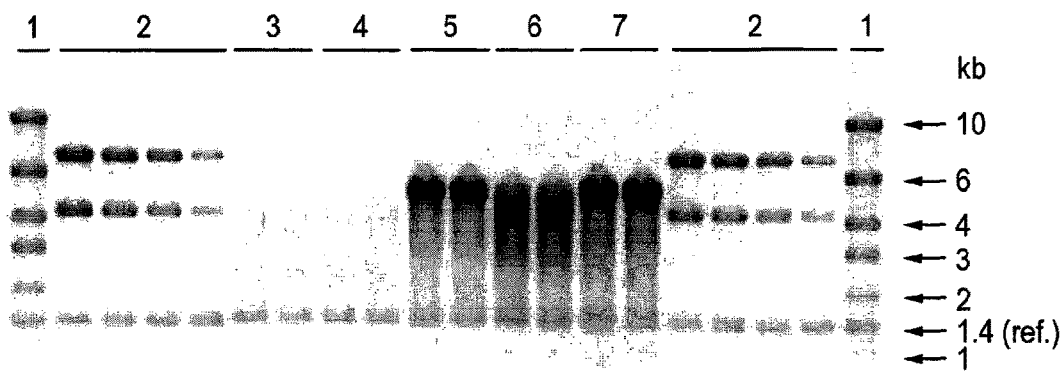
FIG. 4 shows alkaline gel analysis of the rAAV-HLP-codop-hFVIII viral genome derived from: Codop-BDD-hFVIII, group 3=low dose (3e13/ml), group 5=high dose (9e13/ml); Codop-hfFVIII-N6, group 4=low dose (3e13/ml), group 6=high dose (9e13/ml); and Codop-FVIII-V3=group 7 (high dose, 9e13/ml). High Mass DNA Ladder is shown by group 1 and Quantification standard by group 2. A discrete band at ~5 kb is observed with genome extracted from rAAV-Codop-BDD-hFVIII, and rAAV-Codop-FVIII-V3. However the genome in rAAV-Codop-hfFVIII-N6 appears more heterogeneous.
Figure 5:
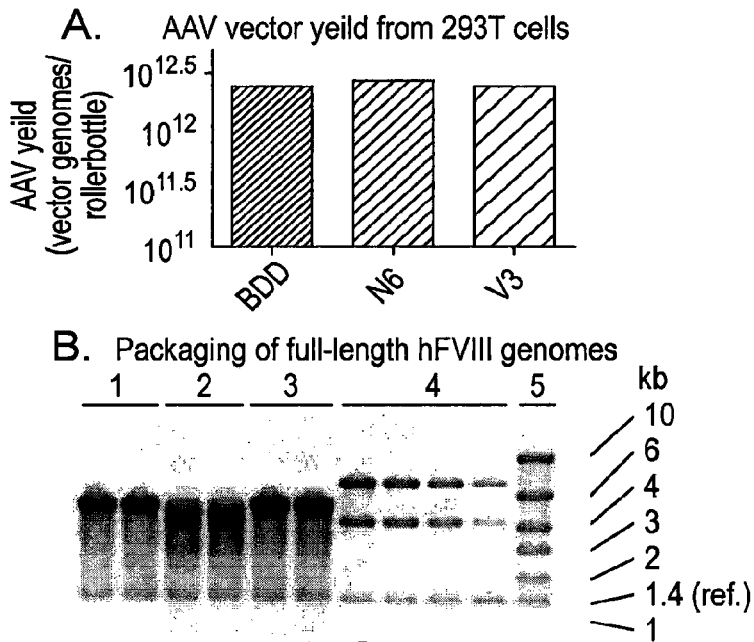
FIG. 5. A: Yield of AAV-HLP-codop-hFVIII variants pseudotyped with serotype 8 capsid B: Alkaline gel analysis of the AAV-HLP-codop-hFVIII viral genome derived from: codop-BDD-hFVIII, (BDD, group 1); codop-N6-hFVIII, (N6, group 2); and codop-FVIII-V3 (V3, group 3). High Mass DNA ladder is shown by group 1 and Quantification standard by group 2. A discrete band at ~5 kb is observed with genome extracted from AAV-codop-BDD-hFVIII, and AAV-codop-FVIII-V3. However the genome in AAV-codop-N6-hFVIII appears more heterogeneous.
Figure 6:
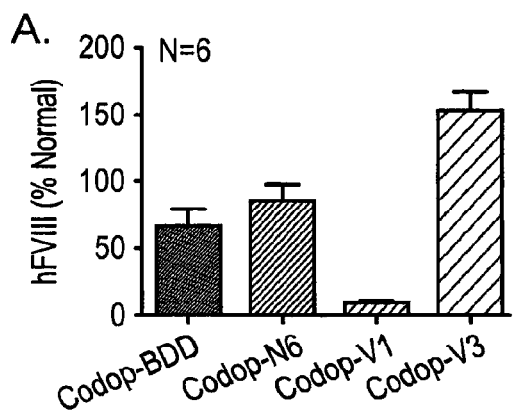
FIG. 6. A: Mean hFVIII levels±SEM in murine plasma after a single tail vein administration of AAV-codop-hFVIII constructs pseudotyped with serotype 8 capsid (dose=$4\times10^{12}$ vg/kg. N=6/group). B: hFVIII expression levels in mice transduced with $2\times10^{13}$ vg/kg corrected for transgene copy number in the liver at 9 weeks after gene transfer.
Figure 6:
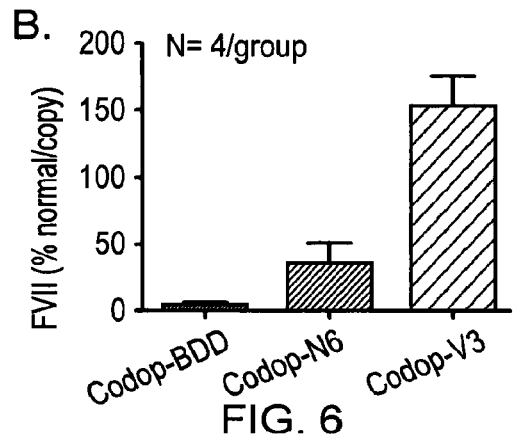
Figure 7:
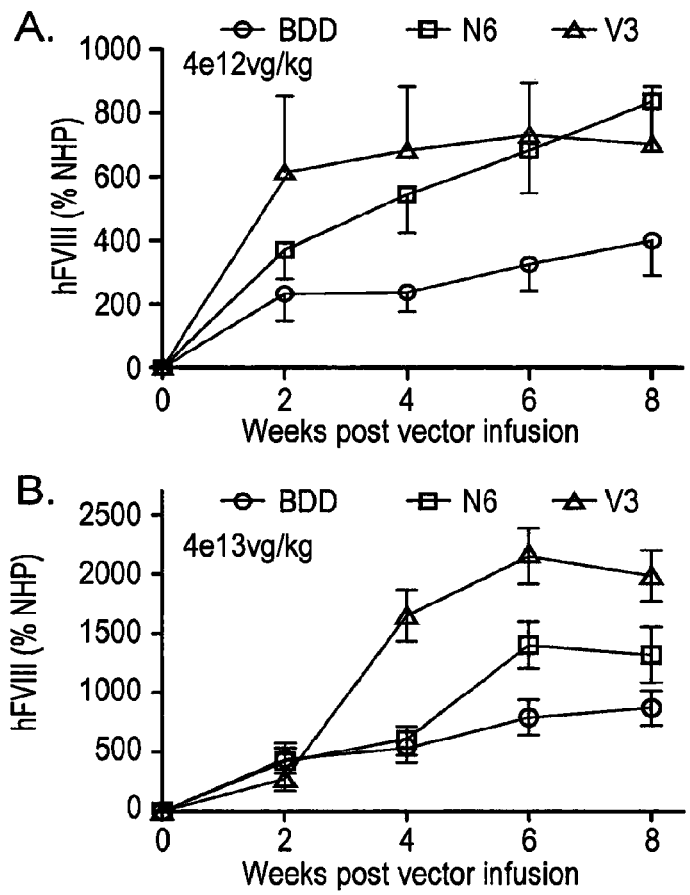
FIG. 7. FVIII activity level in F8−/− mice following a single tail vein administration of low ($2\times10^{13}$ vg/kg, Panel A) or high dose ($2\times10^{14}$ vg/kg, Panel B) of AAV-HLP-codop-hFVIII vectors.
Figure 8:
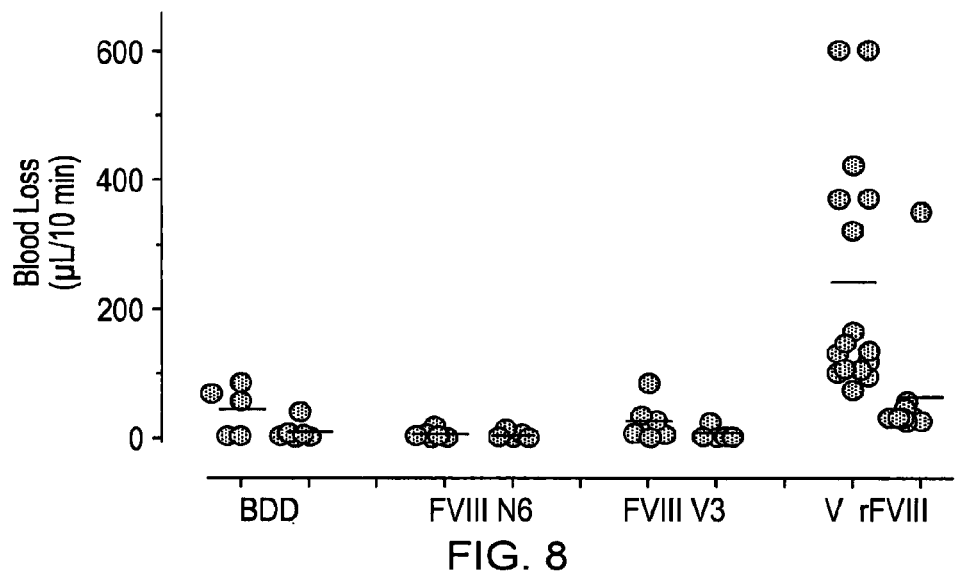
FIG. 8. Blood loss in F8−/− mice following a single tail vein administration of AAV-HLP-codop-BDD-hFVIII (BDD), AAV-HLP-codop-N6-hFVIII (FVIII N6) and AAV-HLP-codop-hFVIII-V3 (FVIII V3) compared to knockout mice treated with vehicle (V) alone or recombinant human FVIII (rFVIII).

The inventors' data show that a rAAV expression cassette encoding the 5.2 kb codop-hFVIII-V3 is packaged uniformly as a full length provirus as shown in FIG. 4. In contrast, the packaging of codop-hFVIII-N6 expression cassette is heterogenous. This is due to the larger size of the codop-hFVIII-N6 expression cassette, which at 5.7 kb significantly exceeds the packaging capacity of AAV. Packaging of heterogenous proviral DNA raises safety concerns because of the potential to synthesis and express truncated forms of FVIII, which could provoke an immunological response.

By shortening the B domain of the codop-hFVIII-N6 variant but retaining essential features of the B domain sequence, in particular the N-linked glycosylation consensus sequences, the inventors have been able to enable more efficient packaging of the transgene into AAV. In the course of creating novel sequences for this purpose, one particular sequence N6V3 proved to be associated with highly efficient packaging into AAV. This sequence also showed a remarkable and unpredicted further improvement of transgene expression in animal gene transfer studies.

Based on rational analysis of the structure of factor VIII and on its known secretion pathway, requiring interaction with the chaperon protein LMANN-1, the inventors have deduced that the expression improvement may be due to the following reasons.

The interaction of factor VIII B domain with the lectin LMANN-1 requires multiple N-linked carbohydrate side chains to be present and for them to adopt a specific conformation for binding between the nascent glycopeptide and the lectin.

The wild type B domain is nearly 1000 amino acids long with no likely secondary structure. Therefore, this lengthy peptide requires a considerable time for synthesis into the Golgi and further time for the random coil to adopt a suitable structure stochastically to bring together the widely separated carbohydrate side chains into a conformation that would enable binding to the lectin (LMANN-1).

By shortening the sequence to the minimum length possible that still retains 6 potential N-glycosylation sites (17 mer), the time required for synthesis is drastically reduced.

Furthermore only a very small number of conformations or possibly just one can occur in the glycosylated peptide amongst which is the required tertiary structure for binding the lectin. The inventors have calculated that the length of this peptide is only just long enough to span the distance between the C-terminal of the A2 domain and the N-terminal of the A3 domain in the crystal structure of B domain deleted factor VIII at 53 Angstroms. Therefore, the N6V3 peptide is further constrained to an almost linear structure that would limit the number of sterically possible conformations and, provided the carbohydrate side chains are added in appropriate places, enable the chaperon to bind virtually co-translationally, thus optimizing to the maximum degree possible this essential step in the factor VIII specific secretion pathway.

The unique specificity of the novel N6V3 sequence is further supported by the fact that very minor deviation from this sequence, such as retaining a single extra amino acid between each N-glycosylation consensus sequence trimer, greatly reduces the synthesis and secretion efficiency of factor VIII compared to that obtained with other versions of the truncated B domain.

A New Shorter Codon Optimised FVIII Variant: Codop-hFVII-V3

The inventors have modified codop-N6-hFVIII, to improve the efficiency with which it is packaged into AAV virions as full length viral genome without compromising its potency in vivo. This involved the replacement of the 226 amino acid B domain spacer with a 31 amino acid (93 bp) peptide, containing a 14 amino acid linker sequence as in B domain deleted FVIII and 17 amino acids which are unique. This peptide contained the 6 asparagine residues present in codop-N6-hFVIII that are required for efficient intra-cellular processing. The peptide brings these residues in closer proximity. Consequently, this new hFVIII variant (AAV-HLP-codop-hFVIII-V3) is 5.1 Kb in size, 600 bp smaller than AAV-HLP-codop-N6-hFVIII (5.7 kb), and closer to the packaging capacity of AAV of approximately 5.0 kb (FIG. 1). AAV-HLP-codop-hFVIII-V1 contains a 44 amino acid peptide that includes the same 6 asparagine residues instead of the 226 amino acid spacer in codop-N6-hFVIII. For comparison another AAV vector (AAV-HLP-codop-BDD-hFVIII, ~5.0 kb in size) was made which contains a codon optimised hFVIII cDNA from which the B domain has been deleted, retaining a small linker sequence of 14 amino acids.

The yield of AAV8-HLP-codop-hFVIII-V3 vector using the standard HEK293 transient transfection method was comparable (FIG. 5) to that of AAV-HLP-codop-N6-FVIII and AAV8-HLP-codop-BDD-hFVIII. Analysis of viral DNA extracted from $2.5\times10^{10}$ particles of each vector preparation following separation on an alkaline agarose gel showed bands of ~5 kb, the expected size for the HLP-codop-BDD-hFVIII (Lane 1, FIG. 5B) and HLP-codop-hFVIII-V3 (Lane 3). In comparison, a rather diffuse signal was observed for the genomes extracted from AAV8-HLP-codop-N6-hFVIII suggesting the packaging of a more heterogeneous proviral species (FIG. 5B, Lane 2).

AAV-HLP-Codop-hFVIII-V3 is More Potent than AAV-HLP-Codop-BDD-hFVIII

AAV vectors containing the different codon optimised FVIII variants, pseudotyped with serotype 8 capsid, were injected as a bolus into the tail vein of 4-6 week old males C57B1/6 mice (N=6) at a dose of $4\times10^{13}$ vg/kg to compare their potency in vivo. The highest level of hFVIII expression was observed with AAV-HLP-codop-FVIII-V3 at 1.52±0.15 IU/ml (152±15% of normal. FIG. 6) 4 weeks after gene transfer. In contrast, AAV8-HLP-codop-N6-hFVIII and AAV8-HLP-codop-BDD-hFVIII mediated hFVIII expression at 0.86±0.11 and 0.67±0.12 IU/ml respectively. The difference in plasma FVIII levels between the AAV8-HLP-codop-BDD-hFVIII and AAV-HLP-codop-hFVIII-V3 cohorts of mice was highly significant (p=0.0015, student T test). The lowest level of hFVII expression was observed with AAV-HLP-codop-hFVIII-V1 (0.10±0.01 U/ml). This is significantly ($p<0.0001$) lower than FVIII expression in the AAV-HLP-codop-hFVIII-V3 cohort of mice, which suggests that the context in which the 6 asparagine residues are brought together in the synthetic B domain amino acid peptide is important. Tail vein administration of a higher dose of vector ($2\times10^{13}$ vg/kg) resulted in between 4-30 fold higher level of plasma hFVIII in the cohort transduced with AAV-HLP-codop-hFVIII-V3 when compared to levels achieved in cohorts of mice transduced with AAV-HLP-codop-N6-hFVIII and AAV-HLP-BDD-hFVIII following correction for transgene copy number (FIG. 6B) in the liver at 9 weeks. The difference in hFVIII levels between AAV-HLP-codop-hFVIII-V3 and AAV-HLP-BDD-hFVIII was highly significant (p=0.0062, student T Test).

Biologic Potency of AAV-HLP-Codop-hFVIII-V3 in F8−/− Mice

A direct comparison of the biologic potency of codop-N6-FVIII, codop-BDD-FVIII and codop-FVIII-V3 was performed in F8−/− mice. Vector encoding each of these FVIII variants, pseudotyped with serotype 8 capsid was administered into the tail vein of male F8−/− mice at a dose of $4\times10^{12}$ (low-dose cohort, n=5/6) or $4\times10^{13}$ (high-dose cohort, n=5/6) vg/kg. For all three constructs the kinetics of expression was broadly similar with plasma hFVIII levels reaching peak levels between 2-6 weeks after gene transfer. For a given construct, hFVIII levels were roughly two fold higher in animals transduced with the high dose of vector when compared to the low dose (FIG. 7). Irrespective of the vector dose, peak hFVIII expression in the cohorts of mice transduced with codop-BDD-hFVIII was approximately two fold lower than observed in animals transduced with codop-N6-hFVIII or codop-hFVIII-V3. At the high dose level the difference in hFVIII expression between the codop-BDD-hFVIII cohort and codop-hFVIII-V3 between weeks 4-8 post gene transfer was highly significant ($p<0.001$ 2 way ANOVA). The average ratio of hFVIII coagulation activity (hFVIII:C) to hFVIII antigen was slightly above 1.0, suggesting the transgenic hFVIII molecules were biologically active.

To establish if the FVIII activity correlated with phenotypic correction in AAV-treated mice, blood loss was analysed by tail clip assay at 8 week after gene transfer (FIG. 8). The amount of blood loss in the AAV-codop-hFVIII-injected mice was almost similar for the 3 codop-hFVIII variants and the two dose levels but substantially lower than observed in FVIII−/− mice treated with vehicle instead of AAV. This difference between AAV and vehicle treated

Figure 9:
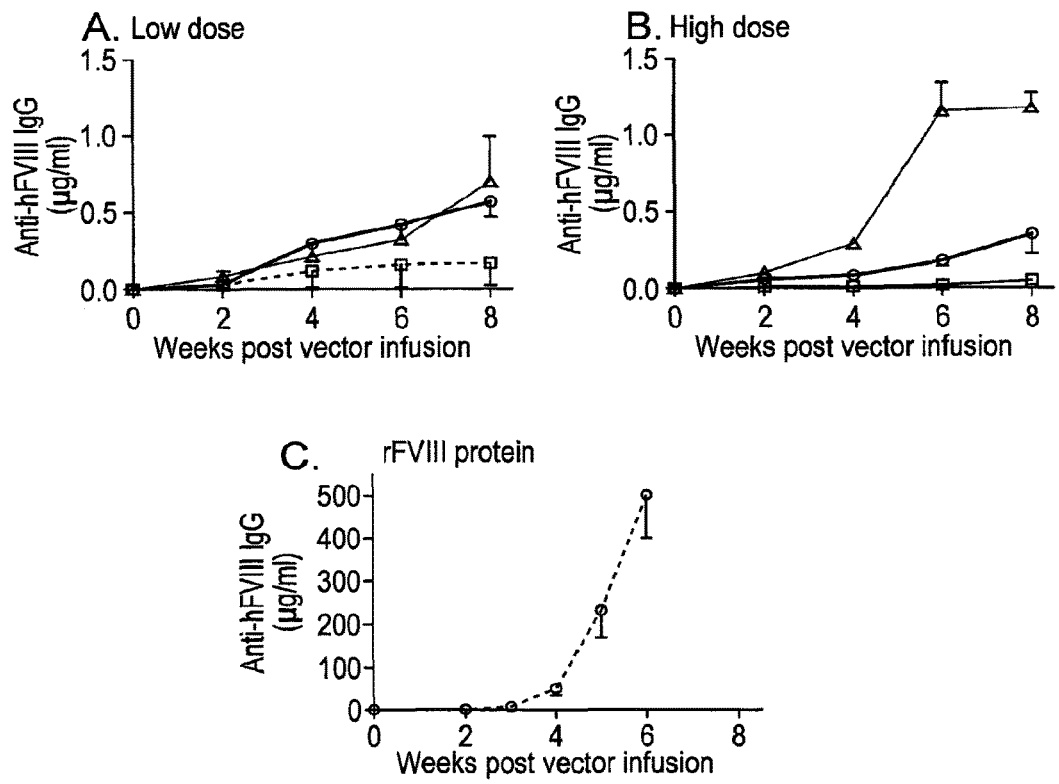
FIG. 9. Anti-hFVIII IgG antibody response. A and B: Anti-hFVIII IgG antibody level following gene transfer with low and high doses of AAV-HLP-codop-BDD-hFVIII (circles). AAV-HLP-codop-N6-hFVIII (squares) and AAV-HLP-codop-hFVIII-V3 (triangles) respectively. C. For comparison anti-hFVIII IgG antibody response following administration of recombinant hFVIII protein is shown.

F8−/− mice was highly significant (p<0.001 one-way ANOVA test). The amount of blood loss in the AAV treated animals was comparable to that observed in F8−/− mice treated with recombinant human FVIII (rFVIII) suggesting that rAAV-mediated expression of FVIII restores haemostasis to levels observed with recombinant FVIII. Anti-hFVIII antibodies were detected over time in all AAV transduced animals with the highest levels being observed in the high dose AAV-HLP-codop-hFVIII-V3 cohort. When compared to the response observed after administration of recombinant hFVIII protein (2 U FVIII per week for 6 weeks) the response in the AAV-codop-hFVIII transduced animals was at least 400 fold lower and insufficient to completely neutralise FVIII activity as illustrated by the tail clip assay (FIG. 9). Consistent with this inhibition of coagulation was not observed when two murine samples with the highest anti-FVIII IgG level were assessed in a Bethesda assay, suggesting that these antibodies do not have neutralising activity.

Figure 10:
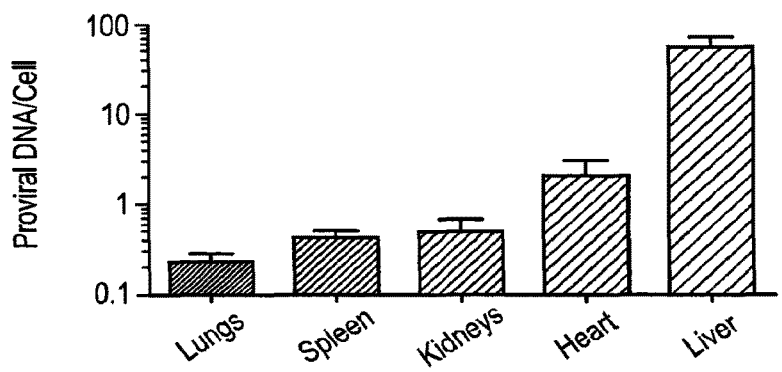
FIG. 10. Biodistribution of vector following peripheral vein administration of $4\times10^{13}$ AAV8-HLP-codop-hFVIII-V3. Results of qPCR analysis of genomic DNA, isolated from the indicated organs at 9 weeks after tail vein administration of $4\times10^{13}$ vg/kg of AAV8 vector using primers unique to codop-hFVIII. Shown is transgene copy number per diploid genome±SE corrected for variation in loading and amplification efficiency using GAPDH primers.

Biodistribution studies (FIG. 10) using a sensitive qPCR based assay demonstrated that the AAV8-HLP-codop-hFVIII-V3 proviral DNA was found predominantly in liver with a mean of 56±15 proviral copies/cell in the $4 \times 10^{13}$ vg/kg cohort of mice at 8 weeks after gene transfer, followed by 2.1±1 copies/cell in the heart, 0.5±0.2 copies/cell in the spleen and kidney and 0.2±0.0.05 in the lungs. The detection limit of QPCR is 0.0003 copy/diploid genome.

Materials and Methods

AAV-hFVIII vector production and purification: The BDD deleted and N6 (kindly provided by Professor Steven Pipe (Miao et al, 2004))-human FVIII variants containing the wild type DNA sequences were cloned downstream of the previously described liver specific LP1 promoter (Nathwani et al, 2006). A 5012 bp codon optimized human N6 FVIII (codop-N6-hFVIII) was generated using codons most frequently found in highly expressed eukaryotic genes, (Haas et al, 1996) synthesized and also cloned downstream of the LP1 promoter. The smaller HLP enhancer/promoter was constructed by synthesizing a 251 bp fragment containing a 34 bp core enhancer from the human apolipoprotein hepatic control region (HCR) upstream of a modified 217 bp alpha-1-antitrypsin (hAAT) gene promoter consisting only of the distal X and the proximal A+B regulatory domains. AAV-HLP-codop-N6-hFVIII was generated by cloning the codop-N6-hFVIII cDNA downstream of the HLP promoter but upstream of a 60 bp synthetic polyadenylation signal. The AAV-HLP-codop-FVIII variants 1 and 3 were made by synthesis of a 1485 and a 1446 bp fragment, respectively. HLP-codop-N6-FVIII was cut with KpnI and the 2028 bp fragment was replaced with the synthesised fragments cut with KpnI. AAV vectors were made by the adenovirus free transient transfection method described before (Davidoff et at, 2004). AAV5 pseudotyped vector particles were generated using a chimeric AAV2 Rep-5Cap packaging plasmid called pLT-RCO3 which is based on XX2 (Xiao et al, 1998) and pAAV5-2 (Chiorini et al, 1999) and similar in configuration to that described before (Rabinowitz et al, 2002). AAV8 pseudotyped vectors were also made using the packaging plasmid pAAV8-2 (Gao et al, 2002). AAV2/5 and 2/8 vectors were purified by the previously described ion exchange chromatography method (Davidoff et al, 2004). Vector genome (vg) titers were determined by previously described quantitative PCR and gel based methods (Nathwani et al, 2001), (Fagone et al, 2012). To determine the size of the packaged genome, vector stocks were run on an alkaline gel as previously described in Fagone et al, 2012.

Animal studies: All procedures were performed in accordance with institutional guidelines under protocols approved by the Institutional and/or National Committees for the care and use of animals in the United States and Europe. FVIII-deficient mice (mixed C57B16/J-129 Sv background with a deletion in exon 16) were bred in-house and used for experiments between 8 and 10 weeks of age. Tail vein administration of rAAV vector particles was performed in 7-10 week old male mice as described before (Nathwani et al. 2001).

Determination of Transduction Efficiency and Vector Biodistribution:

Human FVIII ELISA: Human FVIII antigen levels in murine samples were determined by ELISA using a paired FVIII ELISA kit (Affinity Biologicals, Quadratech, Dorking, UK). Flat-bottomed 96-well plates (NUNC™MAXISORP™, Fisher Scientific, Loughborough, UK) were coated with a combination of two mouse monoclonal antibodies (ESH2 (Sekisui Diagnostica, Axis-Shield, Dundee, UK), and N77110M (Biodesign international, AMS biotechnology, Abingdon, UK)) 50 µl of a 100 µg/mL in 50 mM carbonate buffer pH9.6 at 4° C. overnight, washed with PBS containing 0.05% TWEEN 20™(=PBST), and blocked with 200 µL/well of 6% bovine serum albumin (BSA, Sigma, Pool, UK) in PBST during a 1 hour incubation at 37° C. Standards were made by serial dilutions of murine plasma spiked with recombinant human FVIII, starting concentration 41 U/mL ($11^{th}$ BS 95/608 6.9 IU/mL, NIBSC, South Mimms). Murine samples and standards were diluted 1:10 in kit buffer with 50 µl in duplicates. Following a 2 hour incubation at 37° C., the plates were washed and incubated for a further hour with 100 µl of horseradish peroxidase conjugated goat anti-human FVIII polyclonal secondary antibody. After a final wash step, plates were developed with o-phenylenediamine dihydrochloride peroxidase substrate (Sigma) and the optical density was assessed spectrophotometrically at 492 nm. Probability of statistical difference between experimental groups was determined by one-way ANOVA and paired student t test using GRAPHPAD PRISM™version 4.0 software (GraphPad, San Diego, Calif.). FVIII activity was measured in a two-stage coagulation assay, using human plasma as a standard.

Blood loss assay: Mice were anaesthetized with tribromoethanol (0.15 mL/10 g bodyweight) and 3 mm of the distal tail was cut with a scalpel. The tail was immersed immediately in 50 ml saline buffer at 37° C. and blood was collected for 30 min. Two parameters were monitored: First, time to arrest of bleeding was measured from the moment of transection. Second, collected erythrocytes were pelleted at 1500 g and lysed in $H_2O$. The amount of released haemoglobin was determined by measuring the optical density at 416 nm and using a standard curve prepared upon lysis of 20-100 microliter of mouse blood.

Quantification of vector copy number: Genomic DNA was extracted from murine tissues using the DNEASY™Blood and tissue kit (Qiagen, Crawley, UK), 37 ng of genomic DNA extracted from various murine tissues was subjected to quantitativereal-time PCR using primers which amplified a 299 bp region of codop-hFVIII (5' primer: 5' AAGGACTTCCCCATCCTGCCTGG 3' and 3' primer: 5' GGGTTGGGCAGGAACCTCTGG 3') as described previously (Nathwani et al, 2011).

Detection of anti-human FVIII antibodies: Plasma samples from mice were screened for the presence of antibodies against hFVIII using an ELISA. A 96 well MAXISORP™plate (Nunc) was coated with 50 µL of 2 IU/mL recombinant FVIII in 50 m carbonate buffer pH 9.6 at 4° C. overnight. Plates were washed with PBS-T and blocked with 3% BSA/TBS-T (25 mM Tris, 150 mM NaCl, 5 mM CaCl.sub.2, 0.01% TWEEN™, p117.5). 50 μL of serial dilutions of the plasma samples were prepared in 3% BSA/TBS-T. Following a 2 hour incubation at 37° C., the plates were washed and incubated for a further hour with 100 μl of horseradish peroxidase conjugated goat anti-mouse IgG secondary antibody (A8924, Sigma). After a final wash step, plates were developed with o-phenylenediamine dihydrochloride peroxidase substrate (Sigma) and the optical density was assessed spectrophotometrically at 492 nm. Results were expressed as the end-point titer, defined as the reciprocal of the interpolated dilution with an absorbance value equal to five times the mean absorbance background value.

REFERENCES

Altschul S F. Gish W, Miller W, Myers E W, Lipman D J. (1990) *J Mol Biol*, 215, 403-10.
Altschul S F, Madden T L, Schäffer A A, Zhang J, Zhang Z, Miller W, Lipman D J. (1997) *Nucleic Acids Res*, 25, 3389-402
Bantel-Schaal U, Delius H, Schmidt R, zur Hausen H. (1999) *J Virol*, 73, 939-47
Cerullo V, Seiler M P, Mane V, Cela R, Clarke C, Kaufman R J, Pipe S W, Lee B. (2007) *Mol. Ther*, 15, 2080-2087.
Chao H, Sun L, Bruce A, Xiao X, Walsh C E. (2002) *Mol. Ther*, 5, 716-722.
Chiorini J A, Yang L, Liu Y, Safer B, Kotin R M. (1997) *J Viral*, 71, 6823-33
Chiorini J A, Kim F, Yang L, Kotin R M. (1999) *J Virol*, 73, 1309-19
Chen L, Lu H, Wang J, Sarkar R, Yang X, Wang H, High K A, Xiao W. (2009) *Mol. Ther*, 17, 417-424.
Davidoff A M, Ng C Y, Sleep S, Gray J, Azam S, Zhao Y, McIntosh J H, Karimipoor M, Nathwani A C. (2004) *J Virol Methods*, 12, 209-15.
Fagone P, Wright J F, Nathwani A C, Nienhuis A W, Davidoff A M, Gray J T. (2012) *Hum Gene Ther Methods*, 23, 1-7.
Gao G P, Alvira M R, Wang L, Calcedo R, Johnston J, Wilson J M. (2002) *Proc Natl Acad Sci USA*, 99, 11854-9
Haas J, Park E C, Seed B. (1996) *Curr Biol*, 6, 315-24.
Jiang H, Pierce G F, Ozelo M C, de Paula E V, Vargas J A, Smith P, Sommer J, Luk A, Manno C S, High K A, Arruda V R. (2006) *Mol Ther*, 14, 452-455.
Kaufman R J, Pipe S W, Tagliavacca L, Swaroop M, Moussalli M. (1997) *Blood Coagul. Fibrinolysis*, 8 Suppl 2, S3-14.
Malhotra, J. D., Miao, H., Zhang, K., Wolfson, A., Pennathur. S., Pipe, S. W., & Kaufman, R. J. (2008) Proc. Natl. Acad. Sci. U.S.A, 105, 18525-18530.
Miao C H, Thompson A R, Loeb K, Ye X. (2000) *Mol Ther*, 3, 947-57.
Miao H Z, Sirachainan N, Palmer L, Kucab P, Cunningham M A, Kaufman R J, Pipe S W, (2004) *Blood*, 103, 3412-3419.
Muyldermans S. (2001) *J Biotechnol*, 74, 277-302
Nathwani A C. Davidoff A, Hanawa H, Zhou J F, Vanin E F, Nienhuis A W. (2001) *Blood*, 97, 1258-65.
Nathwani A C, Gray J T, Ng C Y, Zhou J, Spence Y, Waddington S N, Tuddenham E G, Kemball-Cook G, McIntosh J, Boon-Spijker M, Mertens K, Davidoff A M. (2006) *Blood*, 107, 2653-61.
Nathwani A C, Rosales C, McIntosh J, Rastegarlari G, Nathwani D, Raj D, Nawathe S, Waddington S N, Bronson R, Jackson S, Donahue R E, High K A, Mingozzi F, Ng C Y, Zhou J, Spence Y, McCarville M B, Valentine M, Allay J, Coleman J, Sleep S, Gray J T, Nienhuis A W, Davidoff A M. (2011) *Mol Ther*, 19, 876-85.
Needleman S B, Wunsch C D. (1970) *J Mol Biol*, 48, 443-53.
Okuyama T, Huber R M, Bowling W, Pearline R, Kennedy S C, Flye M W, Ponder K P. (1996) *Hum Gene Ther*, 7, 637-45.
Rabinowitz J E, Rolling F, Li C, Conrath H, Xiao W, Xiao X, Samulski R J. (2002) *J Virol*, 76, 791-801.
Rutledge E A, Halbert C L, Russell D W. (1998) *J Virol*, 72, 309-19.
Srivastava A, Lusby E W, Berns K I. (1983) *J Virol*, 45, 555-64.
Wang L, Takabe K, Bidlingmaier S M, Ill C R, Verma I M. (1999) *Proc Natl Acad Sci USA*, 96, 3906-10.
Wu P, Xiao W, Conlon T, Hughes J, Agbandje-McKenna M, Ferkol T, Flotte T, Muzyczka N. (2000) *J Virol*, 74, 8635-47.
Xiao X, Li J, Samulski R J. (1998) *J Virol*, 72, 2224-32.

---

The invention claimed is:

1. A method for administering to a subject a nucleic acid molecule encoding a Factor VIII protein, comprising:
   intravenously administering to the subject a nucleic acid molecule encoding a Factor VIII protein, wherein the Factor VIII protein B domain comprises a spacer that is replaced and wherein the B domain comprises the amino acid sequence set forth in SEQ ID NO:4.

2. The method of claim 1, wherein the B domain of said Factor VIII protein is between 30 and 37 amino acids in length.

3. The method of claim 1, wherein the B domain of said Factor VIII protein is 31 amino acids in length.

4. The method of claim 1, wherein the B domain of said Factor VIII protein comprises the amino acid sequence of SEQ ID NO:5.

5. The method of claim 1, wherein the B domain of said Factor VIII protein consists of the amino acid sequence of SEQ ID NO:5.

6. The method of claim 1, wherein the Factor VIII protein encoded by the nucleic acid molecule comprises domains A1, A2, A3, C1 and C2, and wherein the nucleic acid molecule is codon optimised compared to a corresponding wild type sequence.

7. The method of claim 1, wherein said Factor VIII protein comprises the amino acid sequence of SEQ ID NO:6.

8. The method of claim 1, wherein said nucleic acid molecule encoding said Factor VIII protein comprises the nucleic acid sequence of SEQ ID NO:3.

* * * * *

UNITED STATES PATENT AND TRADEMARK OFFICE
CERTIFICATE OF CORRECTION

Page 1 of 1

PATENT NO. : 10,124,041 B2
APPLICATION NO. : 15/254984
DATED : November 13, 2018
INVENTOR(S) : Amit Nathwani et al.

It is certified that error appears in the above-identified patent and that said Letters Patent is hereby corrected as shown below:

On the Title Page

At item (57), Line 4, "a nucleotides" should be -- a nucleotide --.

Signed and Sealed this
Twenty-first Day of May, 2019

Andrei Iancu
*Director of the United States Patent and Trademark Office*